US006727377B2

United States Patent
Zhang

(10) Patent No.: US 6,727,377 B2
(45) Date of Patent: Apr. 27, 2004

(54) ASYMMETRIC CATALYSIS BASED ON CHIRAL PHOSPHOLANES AND HYDROXYL PHOSPHOLANES

(75) Inventor: Xumu Zhang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/992,551

(22) Filed: Nov. 6, 2001

(65) Prior Publication Data

US 2003/0040629 A1 Feb. 27, 2003

Related U.S. Application Data

(63) Continuation-in-part of application No. 09/377,065, filed on Aug. 19, 1999, now Pat. No. 6,337,406.
(60) Provisional application No. 60/097,473, filed on Aug. 21, 1998.

(51) Int. Cl.$^7$ .................................................. C07F 9/655
(52) U.S. Cl. .............................. 558/73; 558/76; 558/82; 502/155
(58) Field of Search .......................... 558/73, 76, 82; 502/155

(56) References Cited

U.S. PATENT DOCUMENTS

6,043,396 A    3/2000   Sturmer et al. ................ 568/12

FOREIGN PATENT DOCUMENTS

EP           0 501 586 A2 *   9/1992

OTHER PUBLICATIONS

Brunner et al., J. Organometallic Chem. (1991), vol. 413, pp. 55–63.*
Brunner et al. Zeitschrift Fuer naturforschung, B; Chemical Sciences (1996), vol. 51, No. 8, pp. 1201–1212. (Abstract).*
Article titled "Enantioselective Catalysis, 101, Synthesis and Coordination Properties of ("S,4')–(+)–1,2, –Bis(3'4'–dimethoxy–phospholano) benzene, a New Chiral Diphosphane" by Z. Naturforsch, 1996, pp. 1210–1213.

* cited by examiner

Primary Examiner—Taofiq Solola
(74) Attorney, Agent, or Firm—Ohlandt, Greeley, Ruggiero & Perle, LLP

(57) ABSTRACT

Chiral phosphine ligands derived from chiral natural products including D-mannitol and tartaric acid. The ligands contain one or more 5-membered phospholane rings with multiple chiral centers, and provide high stereoselectivity in asymmetric reactions.

14 Claims, 13 Drawing Sheets

L1 (A)

L2 (B')

L3 (A)

L4 (A)

L5 (A)

L6 (B)

L7 (A)

L8 (A')

L9 (B)

L10 (A)

L11 (A)

L12 (A)

L13 (B)

L14 (B)

L15 (B')

L16 (B)

L17 (B)

L22 (B)

L23 (B)

L24 (B')

L25 (B)

L26 (C)

L27 (D)

L28 (C')

L29 (C)

R = H, Me, Et, Cy, Ph, etc.

L30 (C)

L31 (D)

L32 (C)

X = CHIRAL OXAZOLINES, COOH, OMe, OH, SMe, SH, NR'$_2$, PPh$_2$

R = Me, Et, CH₂Ph, etc.

ASYMMETRIC CATALYSIS BASED ON CHIRAL PHOSPHOLANES AND HYDROXYL PHOSPHOLANES

BACKGROUND OF THE INVENTION

This application is a Continuation-In-Part of and claims priority from U.S. application Ser. No. 09/377,065, filed on Aug. 19, 1999 now U.S. Pat. No. 6,337,406 and claims priority from U.S. Provisional Application Ser. No. 60/097,473, filed on Aug. 21, 1998.

FIELD OF THE INVENTION

This invention relates to chiral phospholanes derived from natural products, and asymmetric catalysis using these phospholanes.

DESCRIPTION OF RELATED ART

Many chiral phosphine ligands have been explored for practical application in asymmetric catalysis, but few chiral ligands or motifs are efficient for the synthesis of commercially useful chiral molecules in industry.

Among known chiral phosphines, several are made from electron-donating chiral phospholanes. One example is the Brunner phospholane shown below. Brunner, H., Organometal. Chem. (1987) 328, 71. However, poor enantioselectivities were observed.

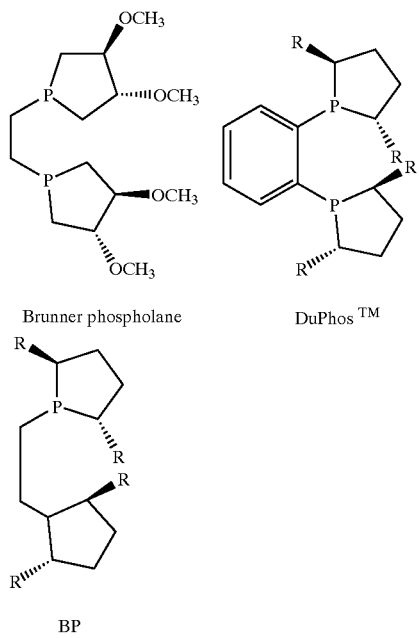

Brunner phospholane

DuPhos™

BP

The ligands DuPhos™ and BPE have been used effectively for certain asymmetric hydrogenation reactions. See U.S. Pat. Nos. 5,329,015; 5,202,493; and 5,329,015; Burk, M. J., J. Am. Chem. Soc. (1991) 113, 8518; Burk, M. J., J. Am. Chem. Soc. (1993) 115, 10125; Burk, M. J., J. Am. Chem. Soc. (1996) 118, 5142. These ligands, however, are not effective for some other asymmetric reactions. Moreover, synthesis of these ligands can be difficult, involving a tedious Kolbe reaction. Also, several liquid DuPhos™/BPE ligands are air-sensitive and therefore difficult to handle.

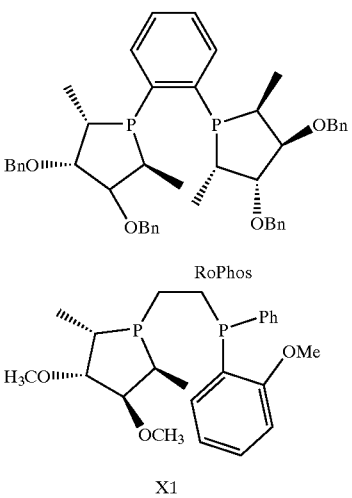

RoPhos

X1

The chiral phosphine RoPhos and its use in Rh-catalyzed asymmetric hydrogenation have been reported. Holz, J. et al., A. J. Org. Chem. (1998) 63, 8031; EP 0889 048. Chiral phosphine X1 has also been reported. Carmichael, D. et al., Chem. Commun. (1999) 261. However, the synthesis is tedious, involving a P stereogenic center.

The inventor has found that it was not possible to make hydroxy analogs of RoPhos using the experimental procedure disclosed in J. Org. Chem. (1998) 63, 8031. A new synthetic route has been developed. Unique properties are associated with hydroxyl phospholanes. An efficient route to these compounds has also been developed by this inventor. Based on this hydroxyl phospholane framework, a polymer chain or a soluble species such as $SO_3^-$, $PO_3^{2-}$, $(CH_2CH_2O)_nCH_2CH_2OH$ (n=1, 2, 3) can be introduced.

SUMMARY OF THE INVENTION

One aspect of the invention is a ligand of formula A, A', B, B', C, C', D, or D', or the corresponding enantiomer:

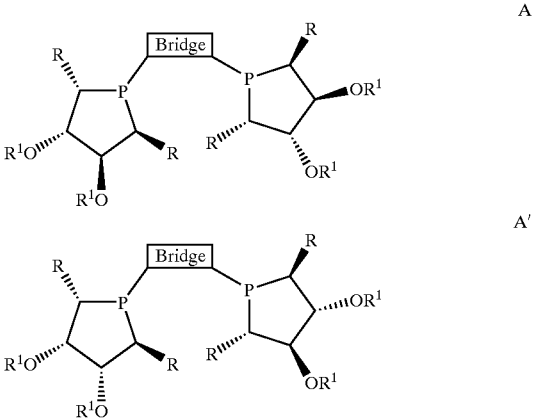

-continued

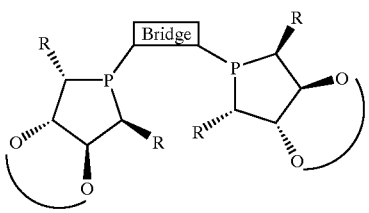

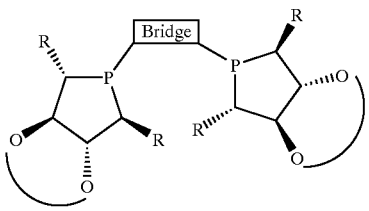

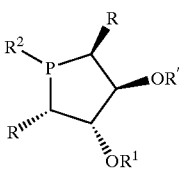

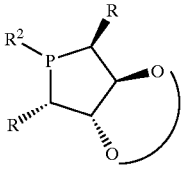

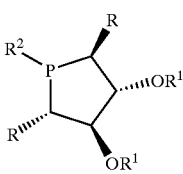

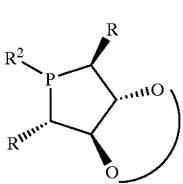

Another aspect of the invention is a compound of formula E:

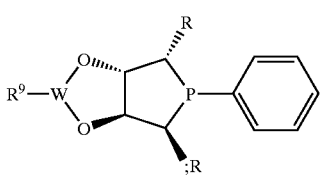

Another aspect of the invention is a catalyst including one of the compounds A–E above, wherein the compound is in the form of a complex with a transition metal.

Another aspect of the invention is a process for preparing a compound of formula B, by reacting a compound of formula $B^x$ with a phosphine:

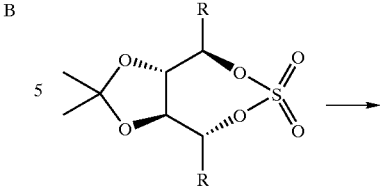

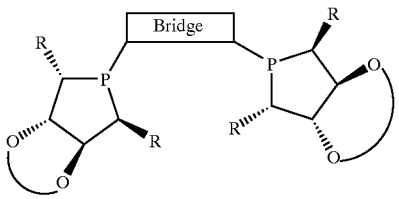

Another aspect of the invention is a process that includes subjecting a substrate to an asymmetric reaction in the presence of one of the above-described ligands, wherein said asymmetric reaction is a hydrogenation, hydride transfer, hydrosilylation, hydroboration, hydrovinylation, olefin metathesis, hydroformylation, hydrocarboxylation, allylic alkylation, cyclopropanation, Diels-Alder, Aldol, Heck, [m+n] cycloaddition, or Michael addition reaction.

Accordingly, one advantage of the invention is in providing chiral ligands that can be made in large scale from inexpensive natural products such as D-mannitol or tartaric acids. Another advantage is in providing new chiral ligands A'–D' in FIG. 3, in which the relative configuration of the four stereogenic centers around the phospholane differs from A–D.

Yet another advantage is in providing chiral ligands that are solid and/or more air-stable due to added functional groups, and are more easily handled compared to air-sensitive liquids such as DuPhos™/BPE ligands. Yet another advantage is in providing chiral ligands that have functional groups on the phospholanes that can be key stereochemistry-defining groups, such as a hemilabile anchor, a hydrogen bonding source, or a cation binding site through a crown ether. Yet another advantage is in providing chiral ligands that have additional functional groups on the phospholanes with water-soluble properties and a convenient site to link a polymer support.

Yet another advantage of the invention is in providing catalysts for a variety of asymmetric reactions such as hydrogenation, hydride transfer reaction, hydrosilylation, hydroboration, hydrovinylation, olefin metathesis, hydroformylation, hydrocarboxylation, allylic alkylation, cyclopropanation, Diels-Alder reaction, Aldol reaction, Heck reaction, Baylis-Hillman reaction and Michael addition can be explored based on these innovative ligand systems.

Yet another advantage of the invention is in providing a variety of methods to make both enantiomers of chiral phosphines. Besides D-mannitol, other chiral pool materials such as D and L-tartaric acids can also be used as suitable starting materials for ligand synthesis. Only one phospholane enantiomer can be conveniently obtained using D-mannitol as the starting material while both phospholane enantiomers can be easily obtained when using D and L-tartaric acids for the ligand synthesis.

Both the foregoing general description and the following detailed description of the invention are exemplary and explanatory only and are not necessarily restrictive of the claimed invention.

DETAILED DESCRIPTION OF THE INVENTION

Figure 1:
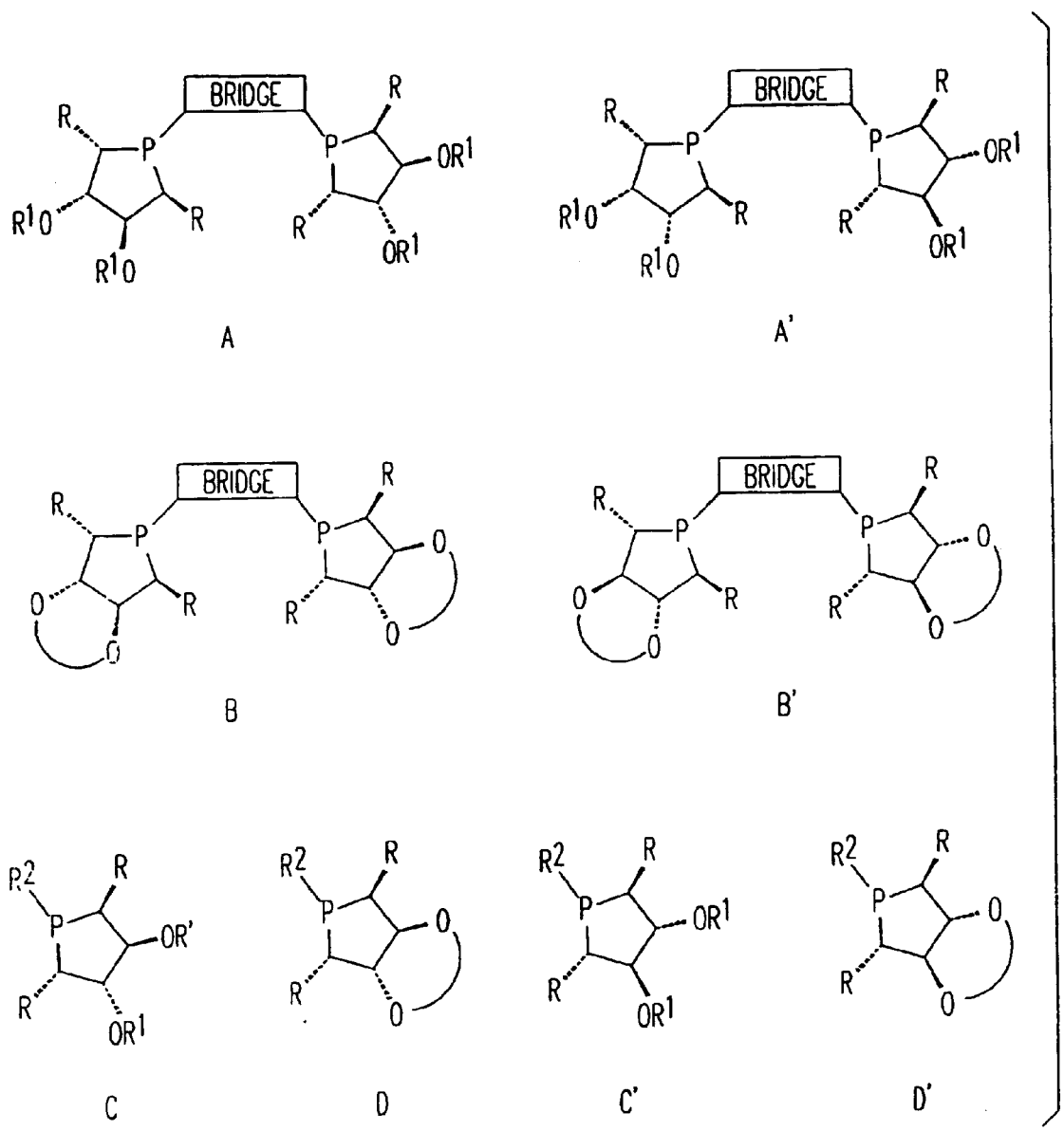
FIG. 1 shows new chiral ligands A, A', B, B', C, C', D, and D' of the invention.

The following definitions are used. Other abbreviations well known to persons of skill in the art of asymmetric synthesis are also used in this specification.

% ee: enantiomeric excess, (% S−% R)/(% S+% R) or (% R−% S)/(% S+% R)

acac: acetylacetonate
Bn: benzyl
COD: 1,5-cyclooctadiene
Cy: cyclohexyl
DBA: dibenzylideneacetone
HMPA: hexamethylphosphoramide
Ipc: isopinocampheyl
MOM: methoxymethyl
Otf: trifluoromethanesulfonate
rt: room temperature
TBDMSCL: t-butyldimethylsilyl chloride
Im: imidazole The chiral ligands of the present invention may contain alkyl and aryl groups. By alkyl is meant any straight, branched, or cyclic alkyl group. The number of carbons in the alkyl group is not particularly limited. Preferably, alkyl refers to C1–C20, more preferably C1–C8, even more preferably C1–C4 alkyl groups. Examples of such alkyl groups include, but are not limited to, methyl, ethyl, propyl, isopropyl, butyl, sec-butyl, tert-butyl, pentyl, isopentyl, tert-pentyl, hexyl, isohexyl, and cyclopropyl, cyclobutyl, cyclopentyl, and cyclohexyl, and isomers of heptyl, octyl, and nonyl. Alkyl groups may be substituted without particular restriction, provided that the substituents do not have an adverse effect on the asymmetric reaction, and are inert to the reaction conditions or are thereby converted in a desirable manner. Examples of such substituents include, but are not limited to, aryl, heterocyclo, alkoxy, halo, haloalkyl, amino, alkylamino, dialkylamino, nitro, amido, and carboxylic ester groups, and any suitable combination thereof.

By aryl is meant any aromatic or heteroaromatic ring, including such rings fused to other aliphatic, aromatic or heteroaromatic rings. Examples of aromatic rings include, but are not limited to, phenyl, naphthyl, anthryl, fluorenyl, indenyl, and phenanthryl. Heteroaromatic rings may contain one or more heteroatoms, preferably one or more atoms of nitrogen, oxygen, or sulfur. Examples of heteroaromatic rings include, but are not limited to, pyrrole, pyridine, quinoline, isoquinoline, indole, furan, and thiophene. Aryl groups may be substituted without particular restriction, provided that the substituents do not have an adverse effect on the asymmetric reaction, and are inert to the reaction conditions or are thereby converted in a desirable manner. Examples of such substituents include, but are not limited to alkyl, aryl, heterocyclo, alkoxy, halo, haloalkyl, amino, alkylamino, dialkylamino, nitro, amido, and carboxylic ester groups, and any suitable combination thereof.

The optical purity of the ligand is preferably at least about 85% ee, more preferably at least about 90% ee, more preferably at least about 95% ee, even more preferably at least about 98% ee, and even more preferably about 100% ee.

As is well known to a person skilled in the art of asymmetric synthesis, a chiral ligand can exist as two enantiomers of opposite configuration. A person skilled in the art will recognize that for any given asymmetric reaction, each enantiomer will produce products of opposite configuration from the other, but with the same conversion and optical purity. In this specification, ligand and product structures are shown for one enantiomer for convenience. Of course, the disclosure also applies to the corresponding enantiomers of opposite configuration, and a person skilled in the art can select the appropriate enantiomer to achieve the desired product configuration.

FIG. 1 shows several classes of chiral phospholanes (A, B, C, D, and A', B', C', D'). The difference between A, B, C, D, and A', B', C', D' is in the inversion of two chiral centers in the middle of the rings. For each class of ligands, enantiomers are also included, which can be made through different chiral pools. A and A' are chiral bidentate phospholanes with four chiral centers. B and B' are chiral bidentate phospholanes with four chiral centers and linked by a ring in the middle of five membered rings. C, D, C', D' are monophospholanes.

Examples of chiral phospholanes according to the invention include, but are not limited to those shown in FIG. 2. Ligand L1 (A) has a benzyl protecting group on the two center hydroxyl groups while ligand L3 has a hydroxyl group. Ligand L2 belongs to class B' with a cyclic ketyl in the center. Ligands L1–L13 contain bridging groups such as $CH_2CH_2$, benzene, ferrocene, biaryl, binaphthyl groups. Ligands L14–L17 are linked to a polymer backbone. Ligands L18–L21 have water soluble groups. In ligands L22–L25, an 18-crown-6 group was introduced. Ligands L26–L27 are monophospholanes containing a variety of groups. Ligands L30–L32 have additional groups as substituents of aryls; some will lead to hemilabile ligands.

One embodiment of the invention is a compound of formula A, A', B, B', C, C', D, or D', or the corresponding enantiomer:

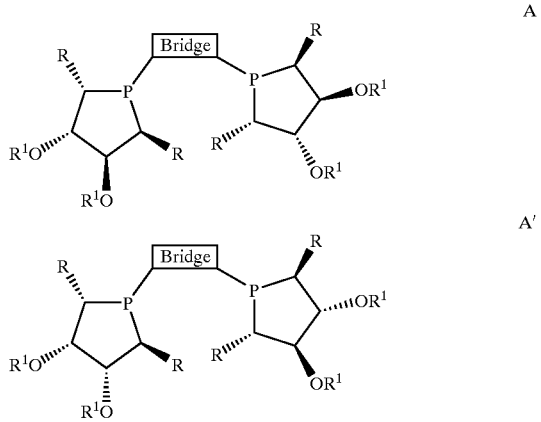

-continued

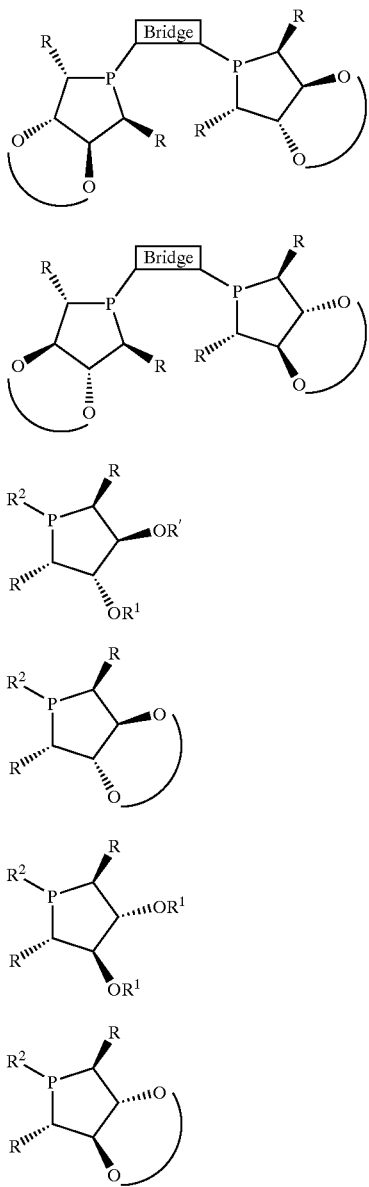

wherein:
a) R and $R^2$ are aryl, alkyl, alkyl aryl, or aryl alkyl, which may be substituted with carboxylic acid, alkoxy, hydroxy, alkylthio, thiol, dialkylamino, diphenylphosphino, or chiral oxazolino groups;
b) $R^1$ can be H, alkyl, silane, aryl, a water soluble unit, or a linked polymer chain or inorganic support;
c) the ring component $\overset{\frown}{O\ O}$ represents a protected diol, a crown ether linkage, —O-alkyl-O— wherein the alkyl group is linked to a polymer, or —O—(CH$_2$CH$_2$—O)$_n$— wherein the methylene groups are optionally substituted by C1–C8 alkyl; and d)

Bridge may be:
—(CH$_2$)$_n$— where n is an integer ranging from 1 to 8;
—(CH$_2$)$_n$X (CH$_2$)$_m$— wherein n and m are each integers, the same or different, ranging from 1 to 8, and X is O, S, $NR^4$, $PR^4$, $AsR^4$, $SbR^4$, divalent aryl, divalent fused aryl, divalent 5-membered ring heterocyclic group, or divalent fused heterocyclic group, wherein $R^4$ is hydrogen, aryl alkyl, substituted aryl or substituted alkyl groups; or
1,2-divalent phenyl, 2,2'-divalent 1,1' biphenyl or 2,2'-divalent 1,2' binapthyl or ferrocene, each of which may be substituted with aryl, C1–C8 alkyl, F, Cl, Br, I, $COOR^5$, $SO_3R^5$, $PO_3R^5_2$, $OR^5$, $SR^5$, $NR^5_2$, $PR^5_2$, $AsR^5_2$, or $SbR^5_2$, wherein:
the substitution on 1,2-divalent phenyl, the ferrocene or biaryl bridge can be independently halogen, alkyl, alkoxyl, aryl, aryloxy, nitro, amino, vinyl, substituted vinyl, alkynyl, or sulfonic acids; and
$R^5$ is hydrogen, C1–C8 alkyl, C1–C8 fluoroalkyl, or C1–C8 perfluoroalkyl, aryl; substituted aryl; arylalkyl; ring-substituted arylalkyl; or —$CR^3_2(CR^3_2)_qX(CR^3_2)_pR^1$ wherein q and p are integers, the same or different, ranging from 1 to 8; $R^3$ is an aryl, alkyl, substituted aryl and substituted alkyl group; and $R^1$ and X are as defined above.

The term "water soluble unit" means any functional group imparting water solubility, including, but not limited to, $SO_3^-$, $PO_3^{2-}$, $CH_2COO^-$, a quaternary ammonium group attached via an ester or alkyl linkage such as C=O(CH$_2$)$_x$NAlk$_3$ or (CH$_2$)$_x$NAlk$_3$ where Alk$_3$ represents three alkyl groups that are independently C1–C4 alkyl and x is 1–4, (CH$_2$CH$_2$O)$_n$CH$_2$CH$_2$OT (n=1–3) wherein T may be H or CH$_3$, i.e., PEG or MeO-PEG. The counterion for water soluble units bearing a charge include, but are not limited to, metals such as alkali and alkaline earth metals, and halogens and Otf.

When $R^1$ is a linked polymer chain, the linker may be any suitable linking unit commonly used to bind catalysts to polymers or support materials, including, but not limited to, a C1–C6 branched or unbranched alkyl chain, —C$_6$H$_4$CH=CH$_2$ for polymerization with styrene or other substituted vinyl monomer, —C=OCH=CH$_2$ for polymerization with an acrylate or other substituted vinyl monomer. The polymer may be any polymer or copolymer, preferably polystyrene or a copolymer of styrene and a substituted vinyl monomer, polyacrylate, PEG or MeO-PEG, or dendritic polymers of polyesters or polyenamides. The preceding also applies to the ring component $\overset{\frown}{O\ O}$ as —O-alkyl-O— wherein the alkyl group is linked to a polymer.

When $R^1$ is a linked inorganic support, examples of inorganic supports include, but are not limited to, silica or zeolites. The inorganic support may be linked by any conventional means, including, but not limited to, attaching —C=ONH(CH$_2$)$_x$Si(OEt)$_3$ (where x is 1–4) as linker and binding through this linker to silica via controlled hydrolysis of the Si(OEt)₃ group, where C=ONH may be replaced by any other functional group suitable for connecting the methylene chain of the linker to the phospholane oxygen.

When the ring component

is a protected diol, a person of skill in the art will recognize that any number of the diol protecting group may be used, e.g., those described in Greene and Wuts, *Protective Groups in Organic Synthesis*, 1991, John Wiley & Sons, and MacOmie, *Protective Groups in Organic Chemistry*, 1975, Plenum Press, the entire contents of which are incorporated herein by reference. A suitable diol protecting group may be deprotected under conditions that do not significantly degrade the rest of the molecule. Examples of diol protecting groups include, but are not limited to acetals and ketals.

In one variant, the invention is a compound of formula A or A', or the corresponding enantiomer. Preferably, in the compound of formula A or A', or the corresponding enantiomer, R is methyl, ethyl, or benzyl, $R^1$ is hydrogen or benzyl, and Bridge is —(CH₂)ₙ— where n is an integer ranging from 1 to 3,1,2-divalent phenyl; 2,2'-divalent 1,1' biphenyl, 2,2'-divalent 1,2' binapthyl, or ferrocene, each of which may be substituted with alkyl having 1–3 carbon atoms; or $OR^5$, wherein $R^5$ is methyl or ethyl.

Examples of the compound of formula A or A' include, but are not limited to L1, L3–L5, L7–L8, L10–L12, and L18–L21, and the corresponding enantiomers, and the compound of formula 2 below and its enantiomer.

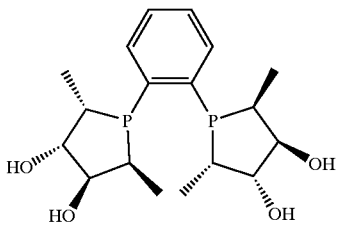

2

In another variant, the invention is a compound of formula B or B', or the corresponding enantiomer. Preferably, in the compound of formula B or B', or the corresponding enantiomer, R is C1–C4 alkyl, unsubstituted or substituted by phenyl or $OR^5$, wherein $R^5$ is C1–C2 alkyl, and the ring component

is —O—$CR^aR^b$—O—, wherein $R^a$ is hydrogen or C1–C4 alkyl and $R^b$ is an alkyl or aryl linker attached to a polymer.

Examples of the compound of formula B or B' include, but are not limited to L2, L6, L9, L13, L14–L17, and L22–L25, and the corresponding enantiomers, and the compound of formula 3 below and its enantiomer:

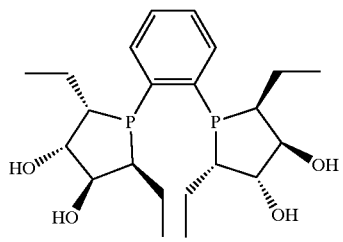

3

In another variant, the invention is a compound of formula C, D, C', or D', or the corresponding enantiomer. Preferably, in the compound of formula C, D, C', or D', or the corresponding enantiomer, R is methyl, ethyl, or benzyl; $R^1$ is hydrogen or benzyl; $R^2$ is o-X-phenyl wherein X is a carboxylic acid, alkoxy, hydroxy, alkylthio, thiol, dialkylamino, diphenylphosphino, or chiral oxazolino group; and the ring component

is —$CR^aR^b$—O—, wherein $R^a$ and $R^b$ are independently hydrogen or C1–C4 alkyl.

Examples of the compound of formula B or B' include, but are not limited to structures L26–L32, and the corresponding enantiomers, and the compound of formula 1 below and its enantiomer:

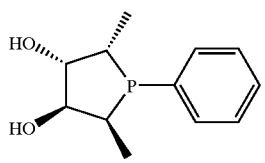

1

Another embodiment of the invention is a compound of formula E or the corresponding enantiomer.

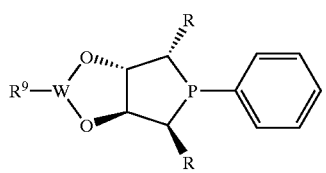

E wherein:
R and $R^9$ are aryl, C1–C8 alkyl, C1–C8 alkyl aryl, or aryl C1–C8 alkyl, which may be substituted with carboxylic acid, alkoxy, hydroxy, alkylthio, thiol, dialkylamino, diphenylphosphino, or chiral oxazolino groups; and
W is boron, phosphorus, or silicon, or W and $R^9$ together form C=O or SO₂.

Preferably, in the compound of formula E or the corresponding enantiomer, R is C1–C4 alkyl and $R^9$ is C1–C4 alkyl or phenyl.

Another embodiment of the invention is a catalyst including any of the compounds described in the embodiments above, wherein the compound is in the form of a complex with a transition metal. In principle, any transition metal may be used. Preferably, the transition metal is a Group VIII transition metal. More preferably, the transition metal is rhodium, iridium, ruthenium, nickel, or palladium. Preferably, the compound is in the form of a complex with $Pd_2(DBA)_3$, $Pd(OAc)_2$; $[Rh(COD)Cl]_2$, $[Rh(COD)_2]X$, $Rh(acac)(CO)_2$; $RuCl_2(COD)$, $Ru(COD)(methylallyl)_2$, $Ru(Ar)Cl_2$, wherein Ar is an aryl group, unsubstituted or substituted with an alkyl group; $[Ir(COD)Cl]_2$, $[k(COD)_2]X$; or $Ni(allyl)X$; wherein X is a counterion. The counterion X may generally be any suitable anion for use in asymmetric synthesis. A person of skill in the art can readily determine what such a suitable counterion would be for any particular set of ligands, reaction conditions and substrates. Examples of suitable counterions include, but are not limited to, halogen ions (including $Cl^-$, $Br^-$, and $I^-$), $BF_4^-$, $ClO_4^-$, $SbF_6^-$, $CF_3SO_3^-$, $BAr_4^-$ (wherein Ar is aryl), and $Otf^-$ (trifluoromethanesulfonate). Preferably, X is $BF_4$, $ClO_4$, $SbF_6$, or $CF_3SO_3$. Preferably, the catalyst comprises $Ru(RCOO)_2(diphosphine)$, $RuX_2(diphosphine)$, $Ru(methylallyl)_2(diphosphine)$, or $Ru(aryl\ group)X_2(diphosphine)$, and X is halogen.

A non-limiting example of the invention is a catalyst for asymmetric hydrogenation of ketones, imines, and olefins, that includes Rh complexes $[Rh(COD)Cl]_2$, $[Rh(COD)_2]X$ (X=$BF_4$, $ClO_4$, $SbF_6$, $CF_3SO_3$, etc.)] with 2 or 3:

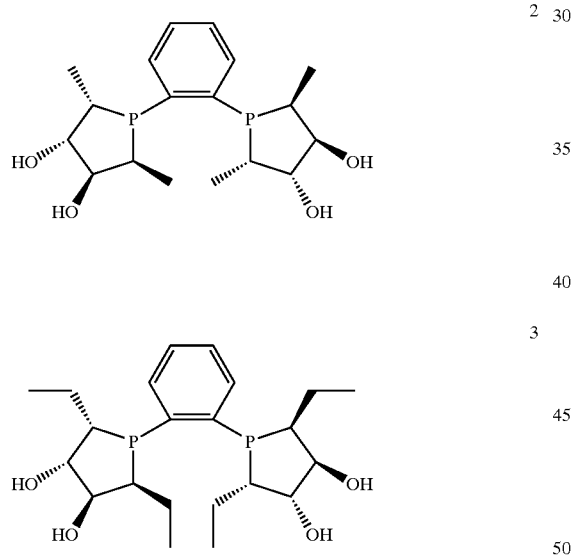

Another embodiment of the invention is a process including subjecting a substrate to an asymmetric reaction in the presence of a catalyst comprising a chiral ligand according to claim 1, wherein said asymmetric reaction is a hydrogenation, hydride transfer, hydrosilylation, hydroboration, hydrovinylation, olefin metathesis, hydroformylation, hydrocarboxylation, allylic alkylation, cyclopropanation, Diels-Alder, Aldol, Heck, [m+n] cycloaddition, or Michael addition reaction. Preferably, the process includes asymmetric hydrogenation of a ketone, imine, enamide, or olefin.

Another embodiment of the invention is a process for preparing a compound of formula B, comprising reacting a compound of formula $B^x$ with a phosphine:

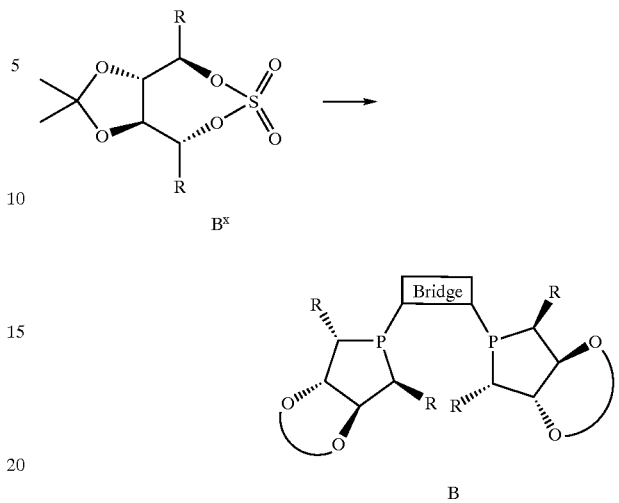

wherein:
the phosphine is

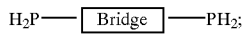

a) R is aryl, alkyl, alkyl aryl, or aryl alkyl, which may be substituted with carboxylic acid, alkoxy, hydroxy, alkylthio, thiol, dialkylamino, diphenylphosphino, or chiral oxazolino groups;

b) the ring component

represents a protected diol, a crown ether linkage, or —O—$CH_2CH_2$)$_n$—O— wherein n is an integer ranging from 1 to 8 and the methylene groups are optionally substituted by alkyl or linked to a polymer; and c)

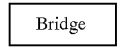

may be:
—$(CH_2)_n$— where n is an integer ranging from 1 to 8;
—$(CH_2)_nX\ (CH_2)_m$— wherein n, m are each integers, the same or different, ranging from 1 to 8; or
1,2-divalent phenyl, 2,2'-divalent 1,1' biphenyl or 2,2'-divalent 1,2' binapthyl or ferrocene, each of which may be substituted with aryl or substituted aryl, or alkyl having 1–8 carbon atoms, heteroatom groups such as F, Cl, Br, I, $COOR^5$, $SO_3R^5$, $PO_3R^5_2$, $OR^5$, $SR^5$, $NR^5_2$, $PR^5_2$, $AsR^5_2$, or $SbR^5_2$, wherein:
the substitution on 1,2-divalent phenyl, the ferrocene or biaryl bridge can be independently halogen, alkyl, alkoxyl, aryl, aryloxy, nitro, amino, vinyl, substituted vinyl, akkynyl, or sulfonic acids; and $R^5$ is hydrogen, C1–C8 alkyl, C1–C8 fluoroalkyl, or C1–C8 perfluoroalkyl, aryl; substituted aryl; arylalkyl; ring-substituted arylalkyl; or —$CR^3{}_2(CR^3{}_2)_qX(CR^3{}_2)_pR^1$ wherein q and p are integers, the same or different, ranging from 1 to 8; X is O, S, $NR^4$, $PR^4$, $AsR^4$, $SbR^4$, divalent aryl, divalent fused aryl, divalent 5-membered ring heterocyclic group, or divalent fused heterocyclic group, wherein $R^3$ and $R^4$ are aryl, alkyl, substituted aryl and substituted alkyl groups.

Preferably, R is C1–C4 alkyl; the ring component

represents a protected diol; and

Bridge is unsubstituted or substituted 1,2-divalent phenyl. More preferably, R is methyl or ethyl, the ring component

is —O—C(CH$_3$)$_2$—O—, and

Bridge is unsubstituted 1,2-divalent phenyl.

Figure 2A:
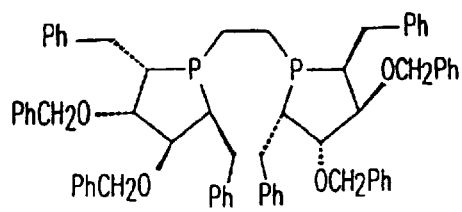
FIGS. 2A–2F shows the structure of ligand examples L1 to L32.
Figure 2A:
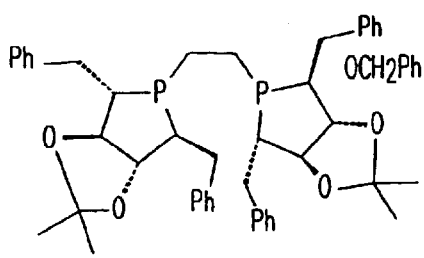
Figure 2A:
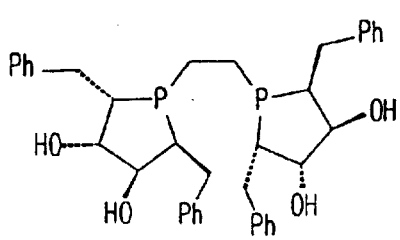
Figure 2A:
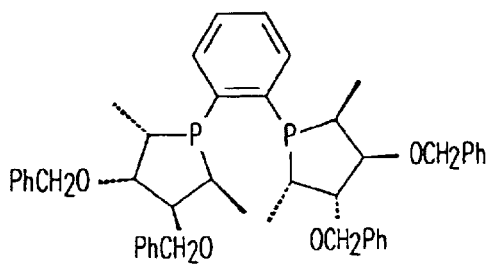
Figure 2A:
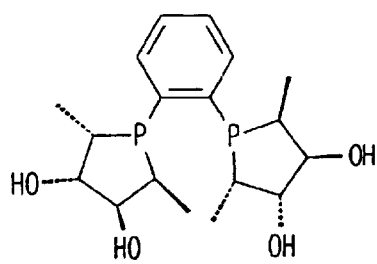
Figure 2A:
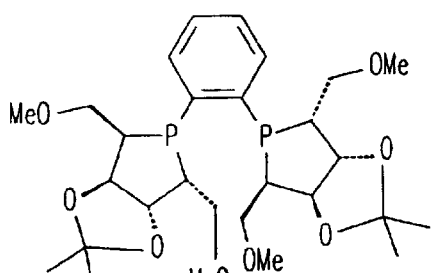
Figure 2A:
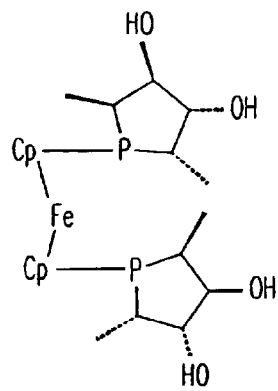
Figure 2A:
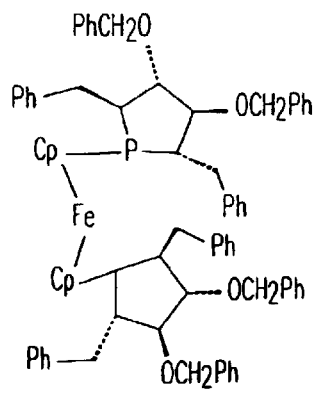
Figure 2B:
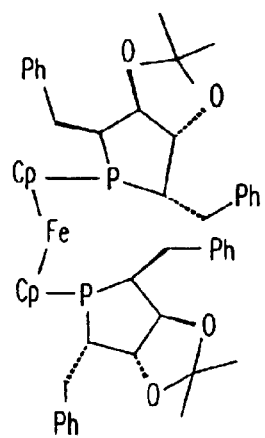
Figure 2B:
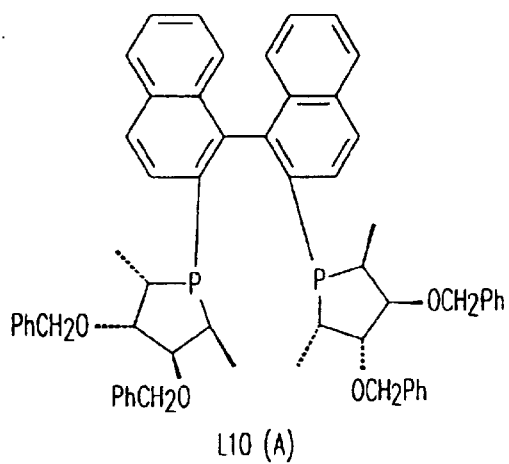
Figure 2B:
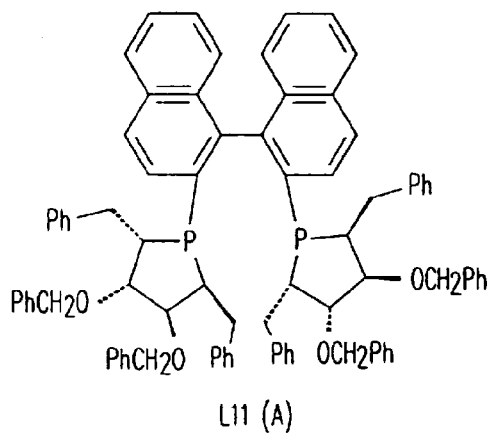
Figure 2B:
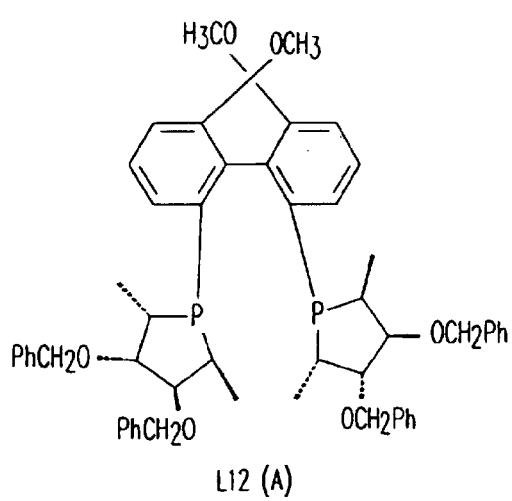
Figure 2B:
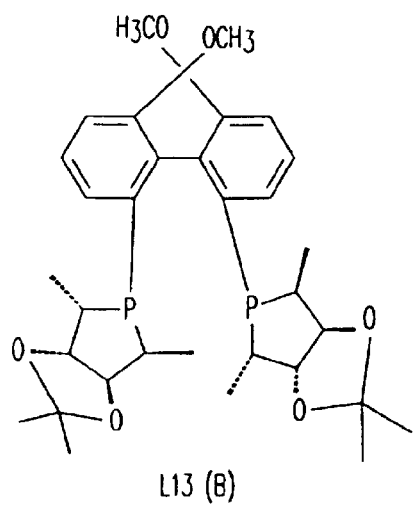
Figure 2C:
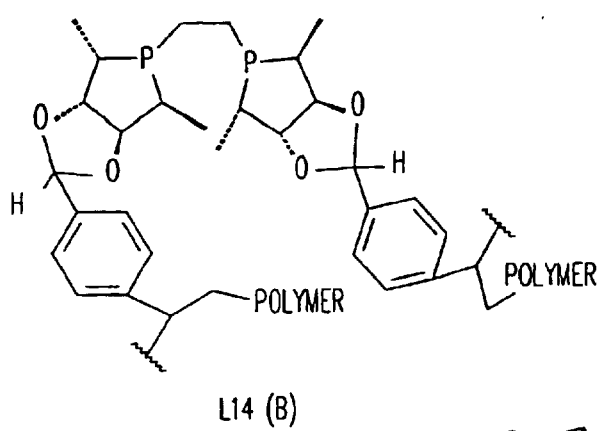
Figure 2C:
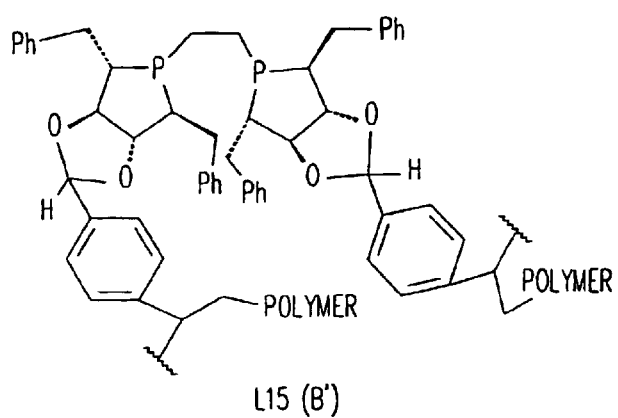
Figure 2C:
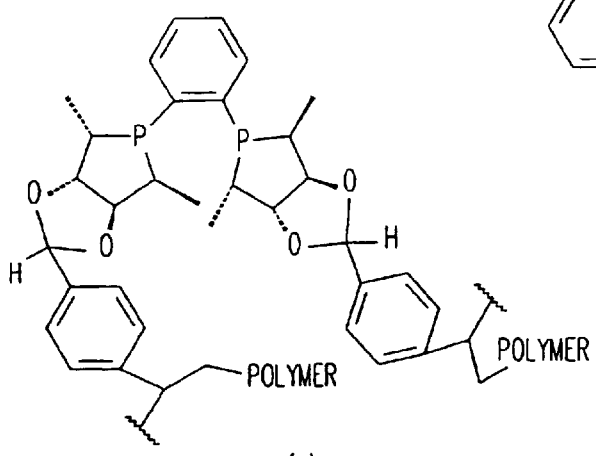
Figure 2C:
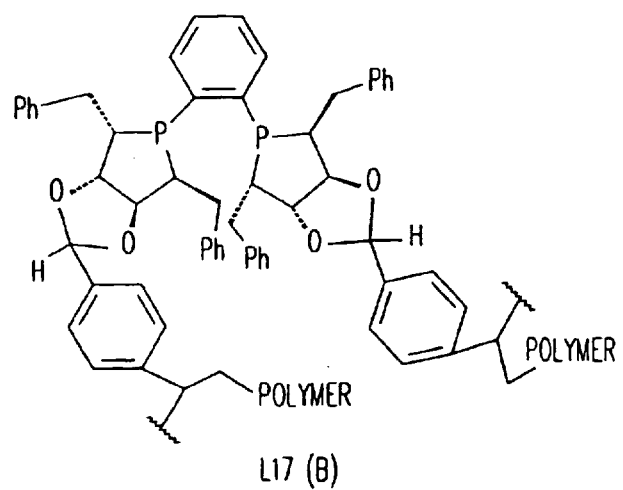
Figure 2D:
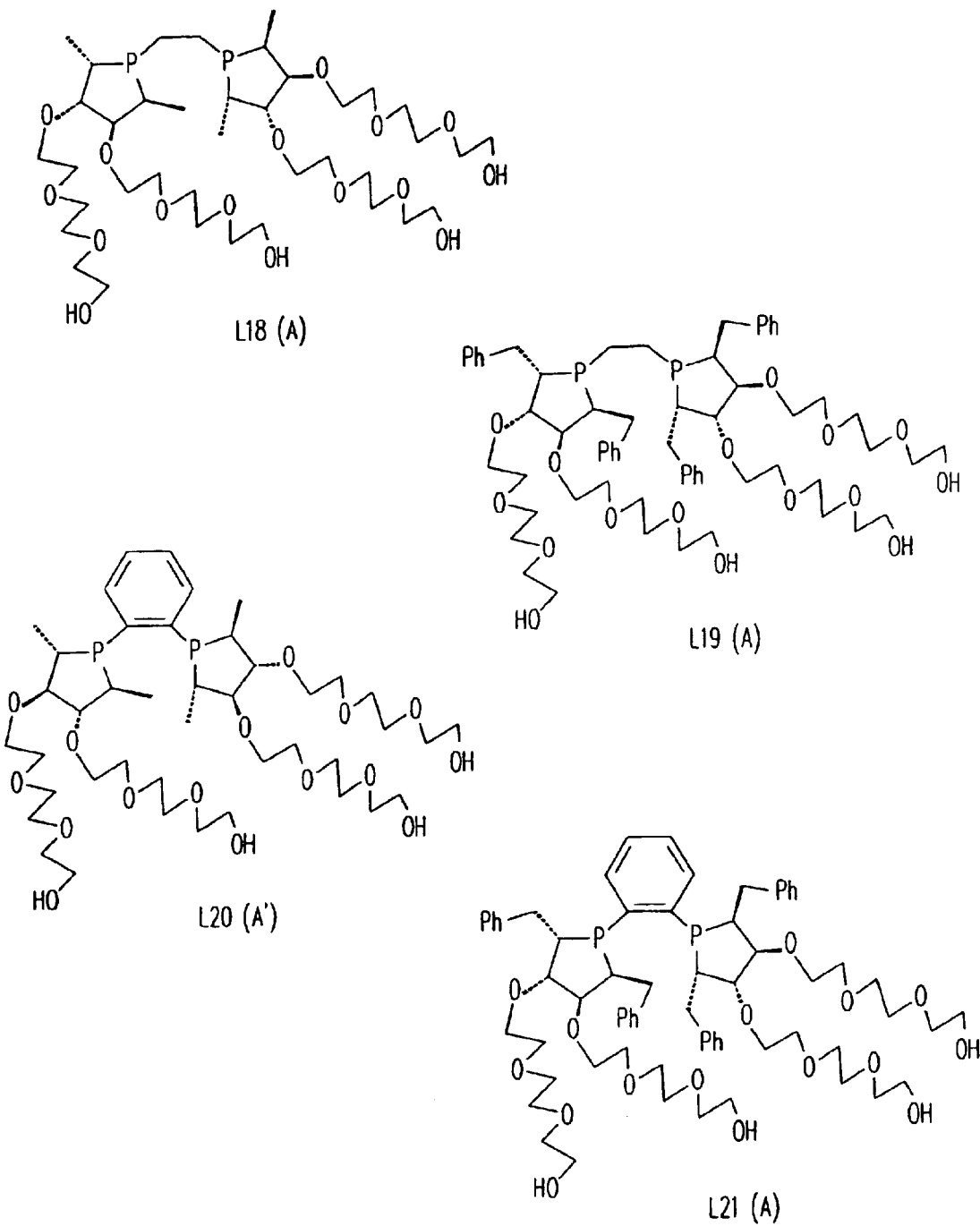
Figure 2E:
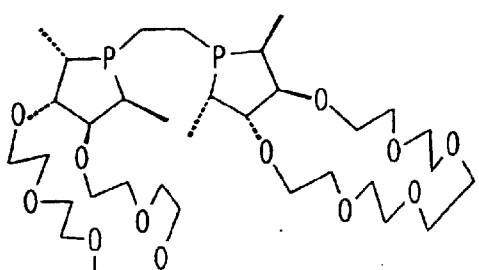
Figure 2E:
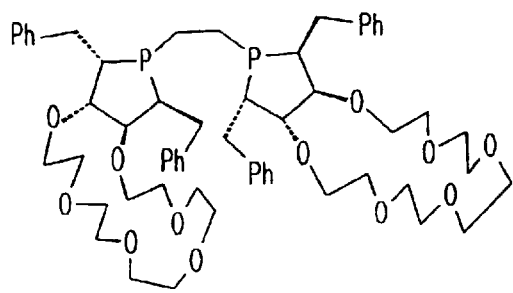
Figure 2E:
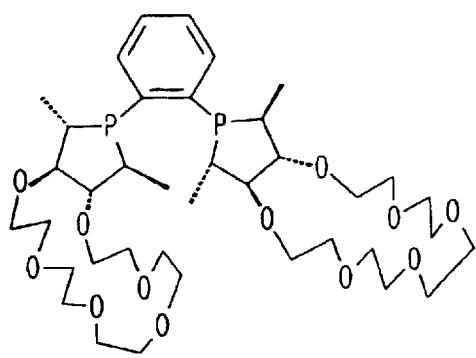
Figure 2E:
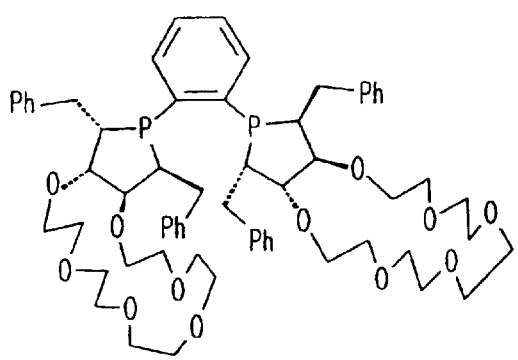
Figure 2F:
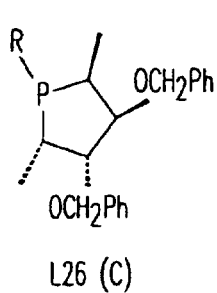
Figure 2F:
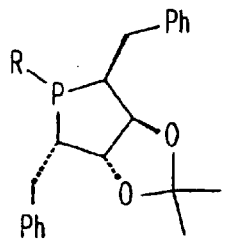
Figure 2F:
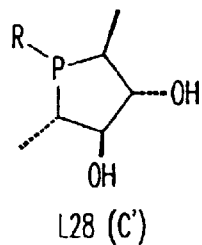
Figure 2F:
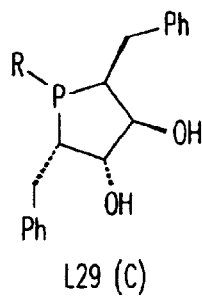
Figure 2F:
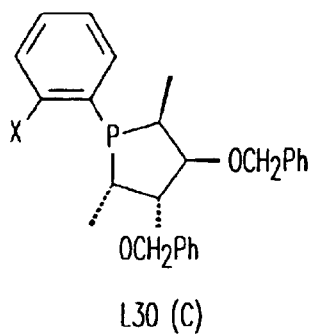
Figure 2F:
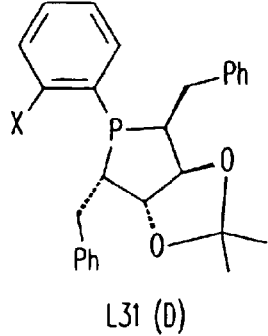
Figure 2F:
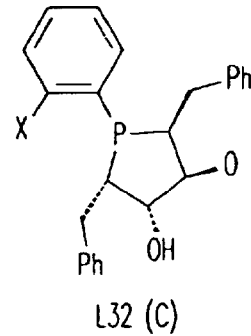
Figure 3A:
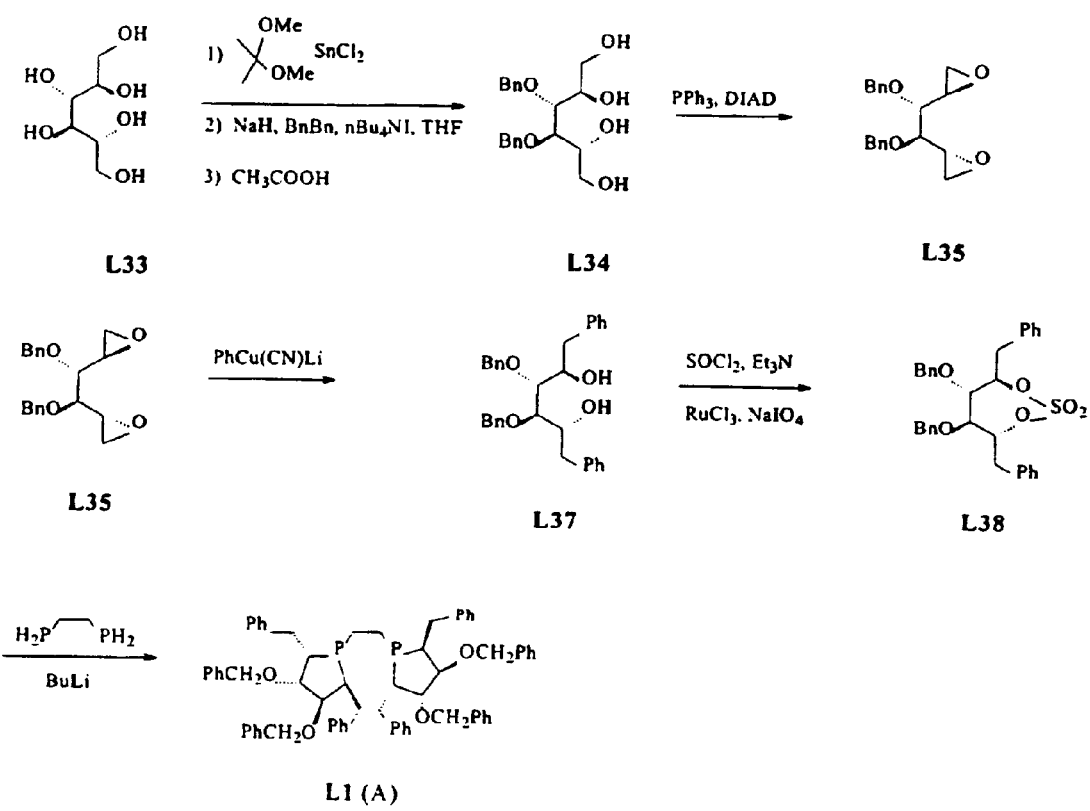
FIGS. 3A–3C illustrate syntheses of ligands L1 to L32.
Figure 3B:
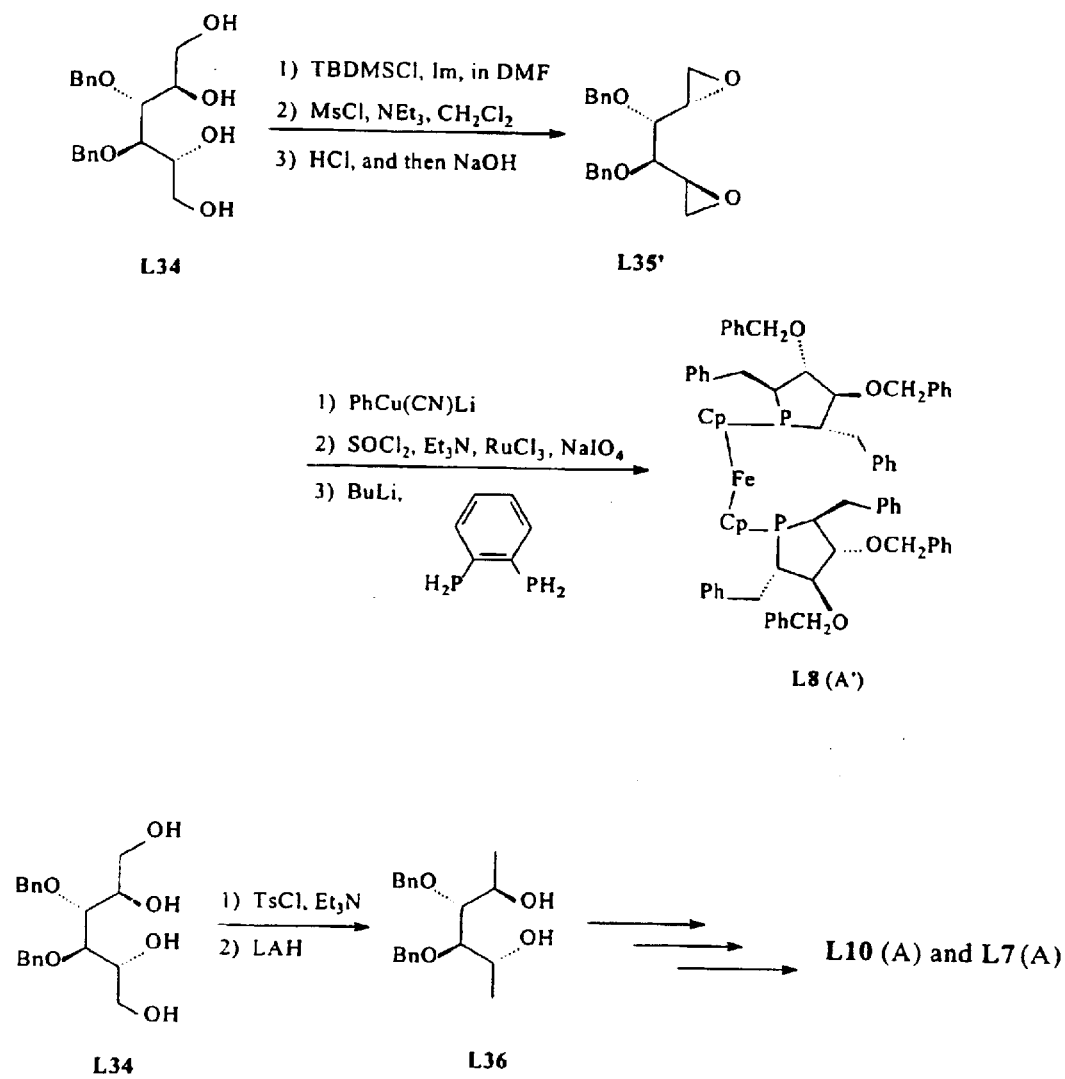
Figure 3C:
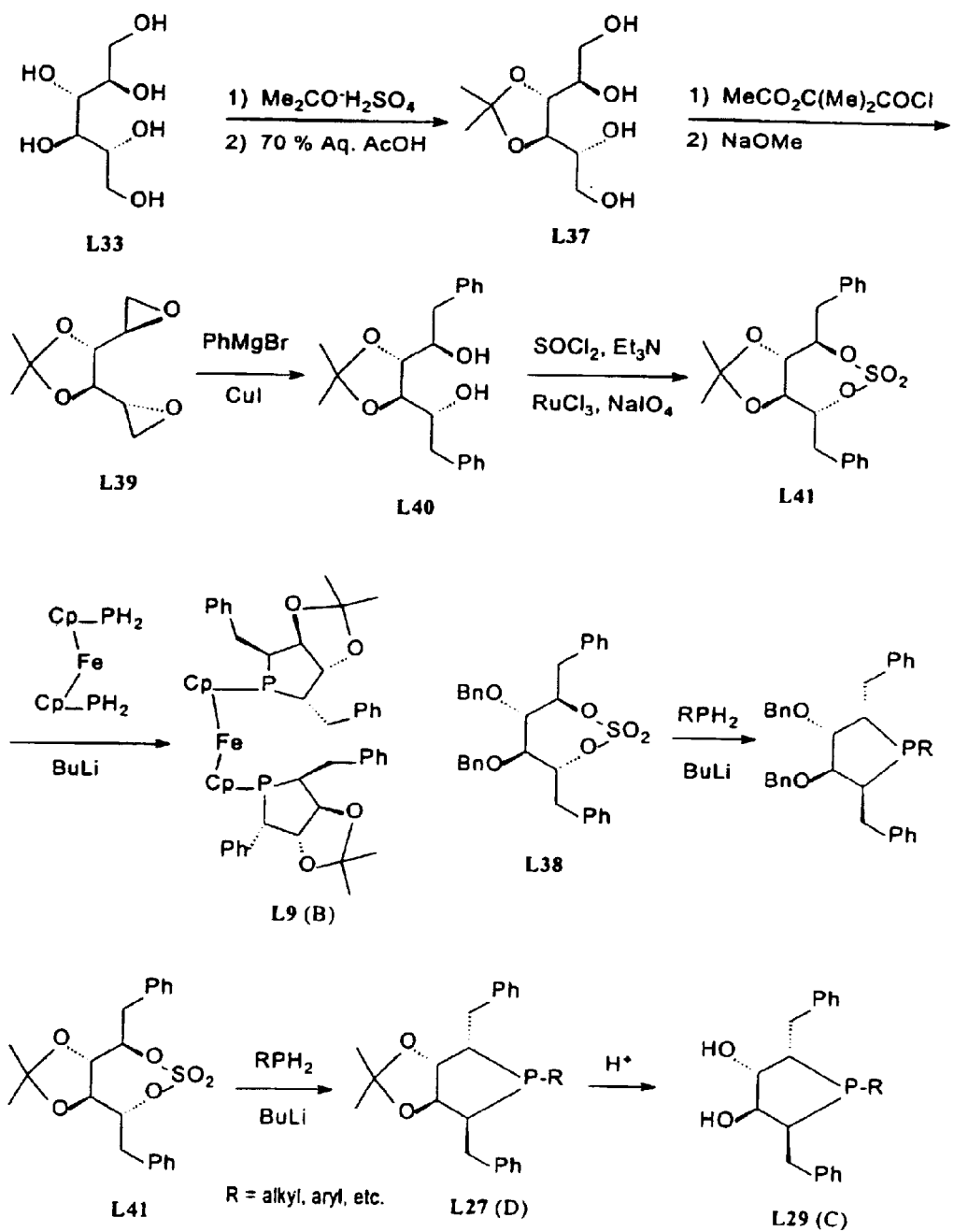

FIGS. 3A–3C show several pathways for the synthesis of compounds shown in FIGS. 2A–2F. The chiral 1,4-diols used in the synthesis of ligands L1–L32 can be derived from D-mannitol and related compounds. A number of these diols have been reported in the literature. The procedure for the synthesis of L1 (A), L3(A) and L8 (A') is outlined in FIGS. 3A–3B; key intermediates L35 and L35' have been reported in the literature (Poitout, L.; Tetrahedron Letter (1994) 35, 3293). The epoxide opening step from L35 to L37 in FIG. 3A has also been reported (Nugel, S. et al. J. Med. Chem. (1996) 39, 2136). Formation of cyclic sulfates can be done according Sharpless' procedure (Kim, B. M., Tetrahedron Letters (1989) 30, 655). The last step is similar as the synthesis of DuPhos™ (Burk, U.S. Pat. Nos. 5,329,015; 5,202,493; and 5,329,015; Burk, M. J., J. Am. Chem. Soc. (1991) 113, 8518; Burk, M. J., J. Am. Chem. Soc. (1993) 115, 10125; Burk, M. J., J. Am. Chem. Soc. (1996) 118, 5142). In the step to form L37, other nucleophiles such as $CH_3{}^-$, $Cy^-$ can be applied other than Ph. Intermediate L36 can be obtained easily. In principle, ketyl can be formed from L3(A) to give class B compounds.

When para-vinyl benzaldehyde is used as the protecting group, polymerization under polystyrene forming conditions should yield compound L17 (B), shown in FIG. 2C.

Instead of using a benzyl protecting group, 18-crown-6 or water soluble groups can be linked to form compounds such as L19 (A) or L25 (B), as shown in FIGS. 2D and 2E, respectively.

Another epoxide L39 has been studied extensively for the synthesis of HIV protease inhibitors (Ghosh, A. K., Tetrahedron Lett. (1991) 32, 5729. and Nugel, S. et al., J. Med. Chem. (1996) 39, 2136). Compound L40 is known and conversion of this intermediate to L9 (B) is expected. Finally, intermediate L41 and L38 can be converted to L29 (C) as illustrated in FIG. 6.

Figure 4A:
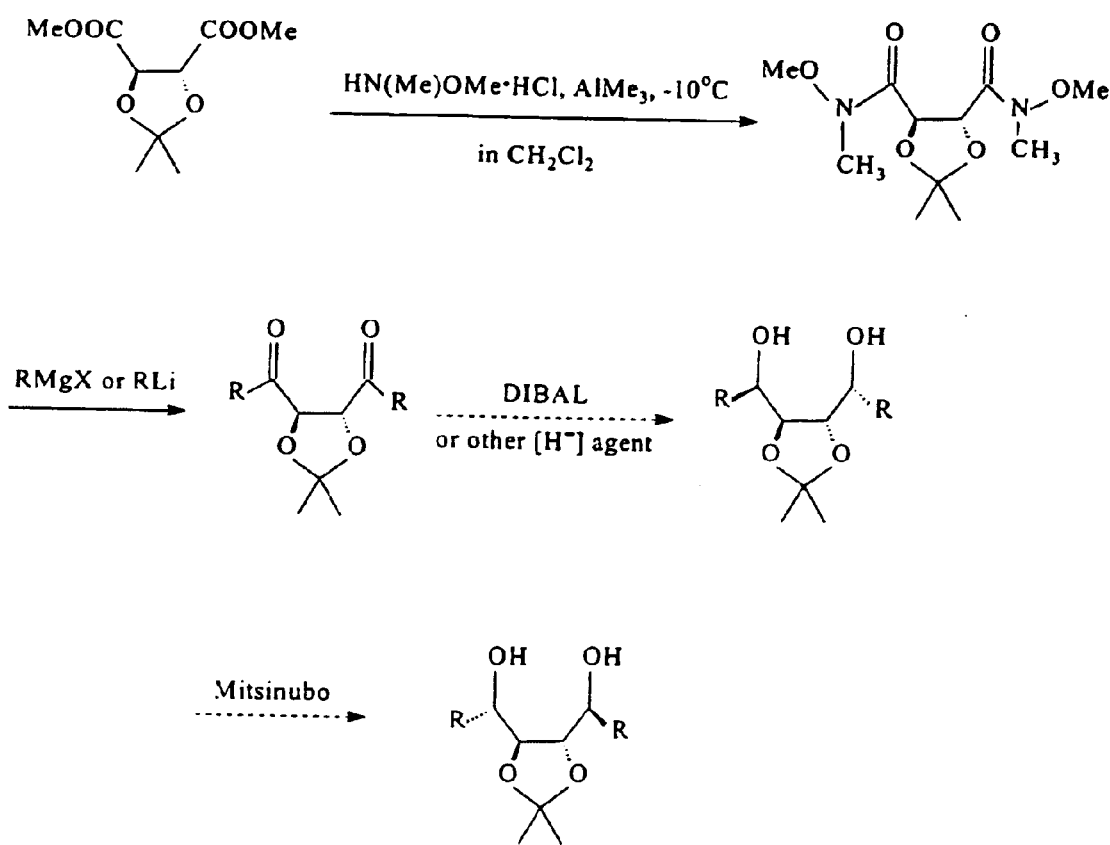
FIGS. 4A–4C show syntheses of some chiral 1,4-diols.
Figure 4B:
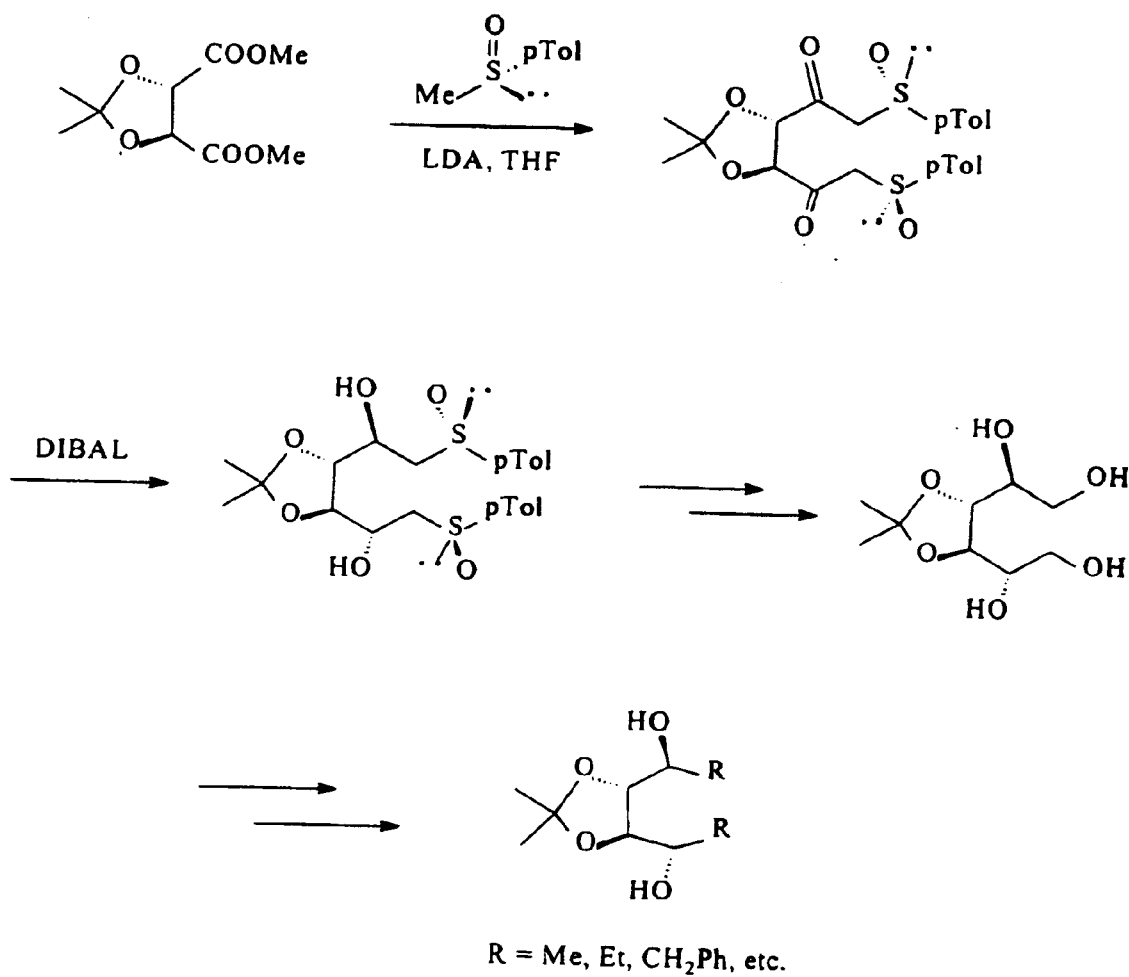
Figure 4C:
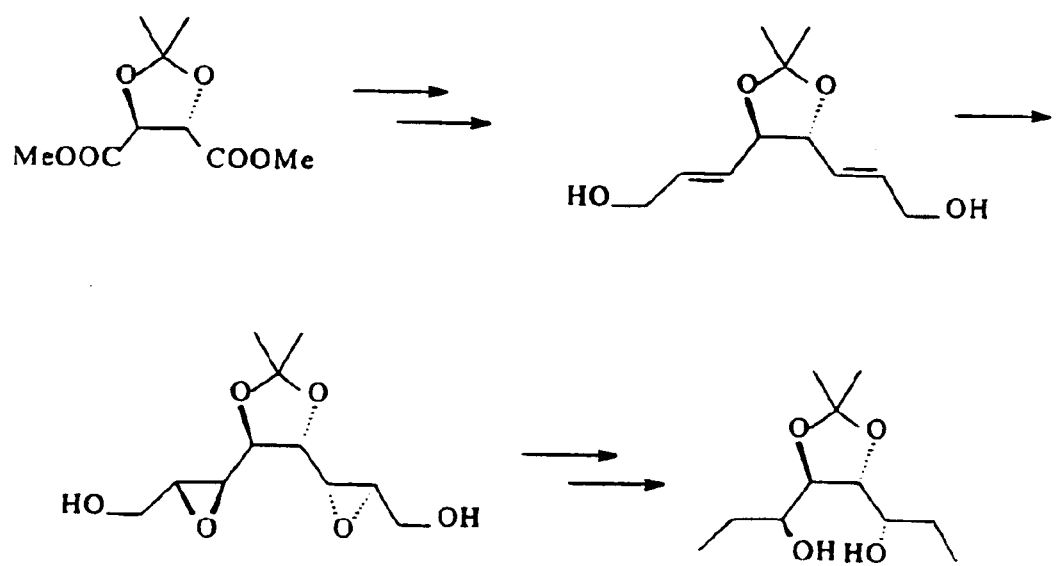

FIGS. 4A–4C outline some useful synthetic procedures, which was recently disclosed in the literature. Instead of using D-mannitol as the starting material, which can only lead to one enantiomer of the chiral phosphine, preparation of chiral diols from either D or L-tartaric ester can result in formation of either of two enantiomers. Using these reported procedures (Nugel, S. et al. J. Med. Chem. (1996) 39, 2136; Colobert, F. J. Org. Chem. (1998) 63, 8918; and Iwasaki, S. Tetrahedron Lett. (1996) 37, 885), several chiral 1,4-diols can be obtained, as shown in FIGS. 4A–4C.

The present invention is further illustrated by the following examples, which are designed to teach those of ordinary skill in the art how to practice the invention. The following examples are illustrative of the invention and should not be construed as limiting the invention as claimed.

EXAMPLES

Synthesis of Phospholane Ligands

The hydroxyl phosphine ligands 1, 2, and 3 were synthesized successfully in high yield using similar procedures. They are white solids. The synthetic route is exemplified below.

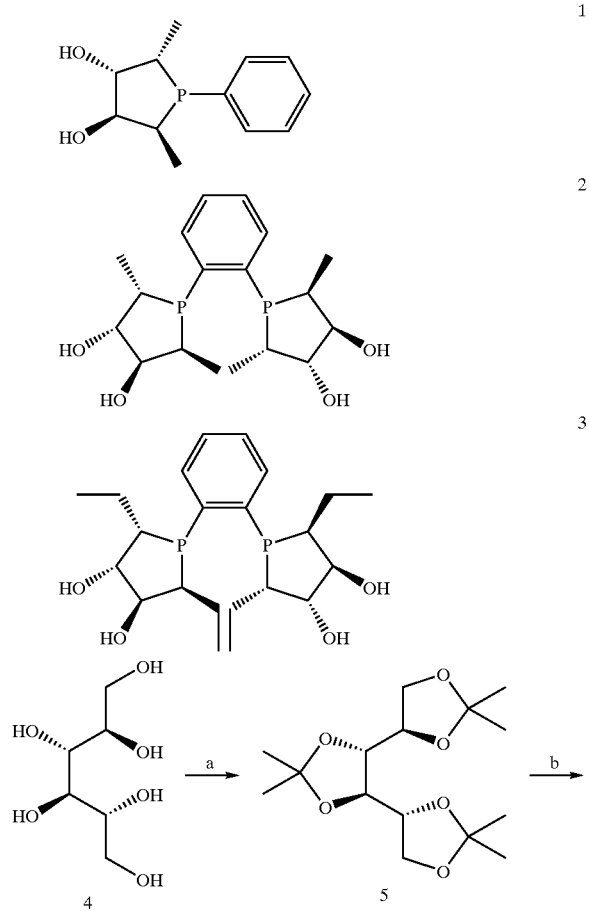

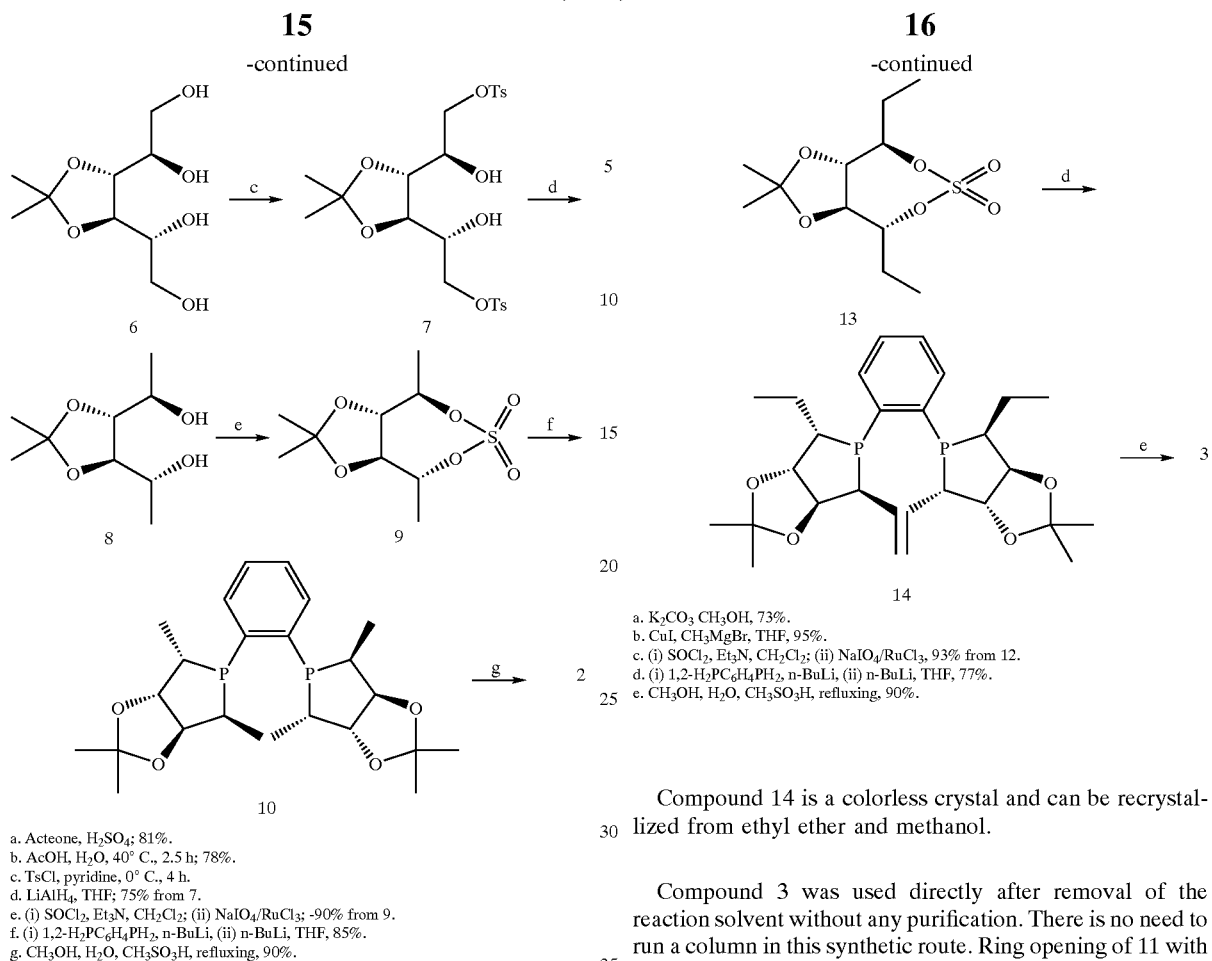

a. Acteone, H₂SO₄; 81%.
b. AcOH, H₂O, 40° C., 2.5 h; 78%.
c. TsCl, pyridine, 0° C., 4 h.
d. LiAlH₄, THF; 75% from 7.
e. (i) SOCl₂, Et₃N, CH₂Cl₂; (ii) NaIO₄/RuCl₃; ~90% from 9.
f. (i) 1,2-H₂PC₆H₄PH₂, n-BuLi, (ii) n-BuLi, THF, 85%.
g. CH₃OH, H₂O, CH₃SO₃H, refluxing, 90%.

Compound 10 is a nice colorless crystal and can be recrystallized from ethyl ether and methanol. Compound 2 was used directly after removal of the reaction solvent without any purification. An advantage of this route is that there is no need to run column chromatography for purification.

a. K₂CO₃ CH₃OH, 73%.
b. CuI, CH₃MgBr, THF, 95%.
c. (i) SOCl₂, Et₃N, CH₂Cl₂; (ii) NaIO₄/RuCl₃, 93% from 12.
d. (i) 1,2-H₂PC₆H₄PH₂, n-BuLi, (ii) n-BuLi, THF, 77%.
e. CH₃OH, H₂O, CH₃SO₃H, refluxing, 90%.

Compound 14 is a colorless crystal and can be recrystallized from ethyl ether and methanol.

Compound 3 was used directly after removal of the reaction solvent without any purification. There is no need to run a column in this synthetic route. Ring opening of 11 with other nucleophiles R₂CuLi (R=Ph, Et, iPr etc.) leads to a series of compounds.

The cyclic sulfate 15 was also made from the corresponding alcohol, which was synthesized in the same procedure to make 12.

Ligand 16 can be made in a similar manner using the same procedure as for the synthesis of 2 and 3.

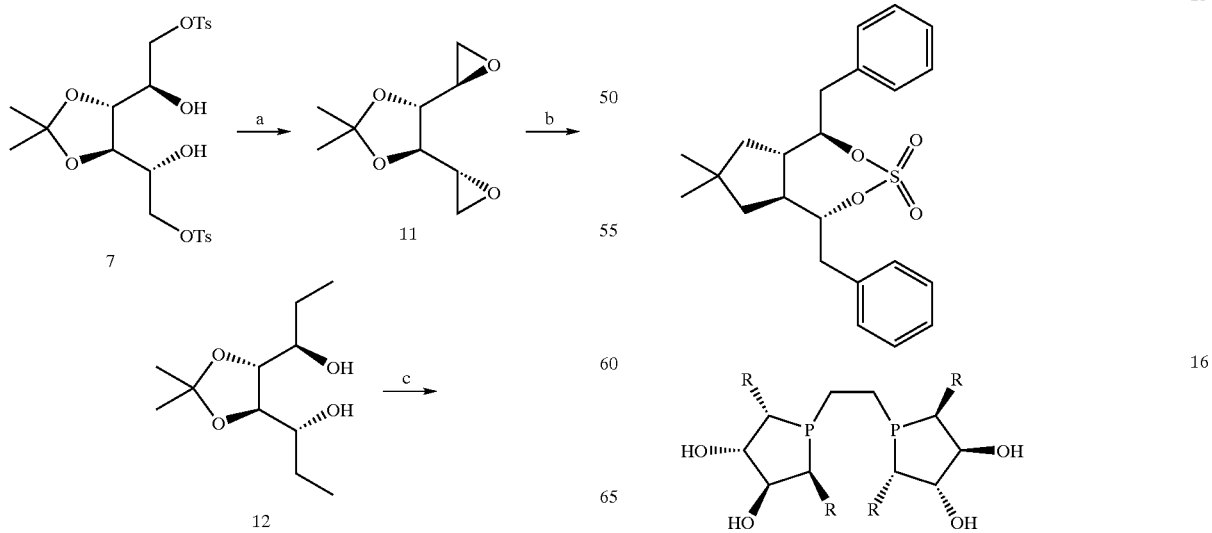

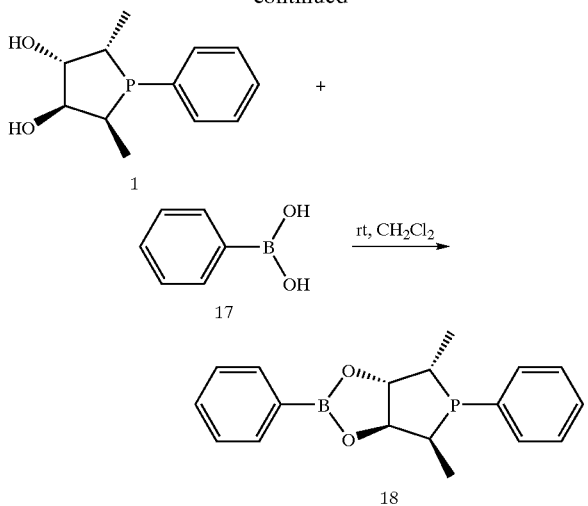

Compound 18 was prepared by stirring 1 and phenylboronic acid in methylene chloride. After removal of the solvent, it was used directly in asymmetric reaction.

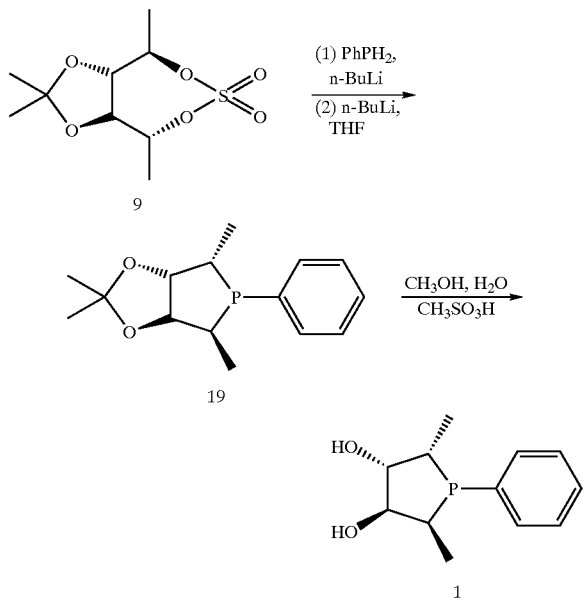

Compound 19 was prepared from cyclic sulfate 9. Acid catalytic hydrolysis afforded the hydroxyl phosphine 1 in high yield (>90%).

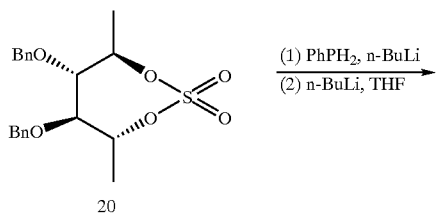

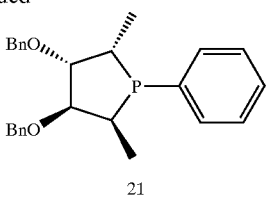

Compound 21 was prepared from known cyclic sulfate 20. Several chiral monophospholanes from D-mannitol (e.g., 19, 21) are made and many methods cleave the protecting groups to give hydroxyl phospholane 1. The iso-propylene group in 19 was smoothly removed by an acid catalyzed hydrolysis. However, the borane adduct of 21 was just selectively debenzylated when $BCl_3$ or $BF_3.Et_2O$ was used as the reagent to give the derivatives bearing one hydroxyl and one benzyl ether group. Hydrogenation of 21 using Pd/C catalyst does not give the desired hydroxyl phospholane product 1. The corresponding phosphine oxide of 21 also gave selectively debenzylated products under mild hydrogenation conditions (10% $Pd(OH)_2$/C). The hydrogenation reaction done under high temperature (50° C.) and $H_2$ pressure (40 atm) not only cleaved the benzyl ether but also reduced the phenyl group to a cyclohexyl group.

General Experimental Procedure

Unless otherwise indicated, all reactions were carried out under nitrogen. THF and ether were freshly distilled from sodium benzophenone ketyl. Toluene were freshly distilled from sodium. Dichloromethane and hexane were freshly distilled from $CaH_2$. Methanol was distilled from magnesium and $CaH_2$. Reactions were monitored by thin-layer chromatography (TLC) analysis. Column chromatography was performed using EM silica gel 60 (230–400 mesh).

$^1H$ NMR were recorded on Bruker ACE 200, WP 200, AM 300 and WM 360 spectrometers. Chemical shifts are reported in ppm downfield from tetramethylsilane with the solvent resonance as the internal standard ($CDCl_3$, $\delta 7.26$ ppm). $^{13}C$, $^{31}P$ and $^1H$ NMR spectra were recorded on Bruker AM 300 and WM 360 or Varian 200 or 500 spectrometers with complete proton decoupling. Chemical shifts are reported in ppm downfield from tetramethylsilane with the solvent resonance as the internal standard ($CDCl_3$, $\delta 77.0$ ppm). Optical rotation was obtained on a Perkin-Elmer 241 polarimeter. MS spectra were recorded on a KRATOS mass spectrometer MS 9/50 for LR-EI and HR-EI. GC analyses were carried out on a Hewlett-Packard 5890 gas chromatograph with a 30-m Supelco β-DEXTM column. HPLC analyses were carried out on a WatersTM 600 chromatograph with a 25-cm CHIRALCEL OD column.

EXAMPLE 1

Phosphine 19

To a stirred solution of phenylphosphine (0.44 g, 4.0 mmol) in THF (80 mL), n-BuLi (1.6 M n-hexane solution, 2.5 mL, 4.0 mmol) was added dropwise via a syringe at −78° C. The resulting pale yellow solution was stirred for further 2 h at room temperature. After cooling the mixture to −78° C., cyclic sulfate 9 (1.01 g, 4.0 mmol) in THF (40 mL) was added over 10 min. The resulting yellow solution was warmed to room temperature and stirred for 4 h. After cooling to −78° C., n-BuLi (1.6 M solution in n-hexane, 2.5 mL, 4.0 mmol) was added, and the reaction mixture was stirred for an additional 20 h at room temperature. The color of the reaction mixture changed from orange yellow to red, and then decolorized to colorless. After removal of the solvent under reduced pressure, the residue was dissolved in 40 mL of ethyl ether, and 30 mL of brine was added. The aqueous layer was then washed with 3×30 mL ethyl ether. The combined organic layers were dried over $Na_2SO_4$ and concentrated to afford a colorless oil. This oil can be further purified by a short silica gel column eluted with hexane/ether (9:1), $^1$H NMR (CDCl$_3$): δ7.72–7.27 (m, 5H, aromatic), 4.60–4.32 (m, 2H), 2.70–2.51 (m, 2H), 1.52 (s, 6H), 1.38–1.32 (m, 3H), 0.70–0.52(m,31). $^{31}$P NMR (CDCl3): δ50.2 ppm.

EXAMPLE 2

Phosphine 1

Phosphine 19 obtained above was dissolved in 50 mL methanol and 2 mL of water. To this solution, 0.05 mL of methanesulfonic acid was added and the resulting mixture was refluxing for 10 h. The solvent was removed under reduced pressure and the residue was dissolved in 50 mL of methylene chloride. 30 mL of aq $NaHCO_3$ was added and the two layers were separated. The aqueous layer was washed with 3×40 mL of methylene chloride. The combined organic layers were dried over $Na_2SO_4$ and concentrated to give a white solid, compound 1.

EXAMPLE 3

Phosphine 21

To a stirred solution of phenylphosphine (220.2 g, 2.0 mmol) in THF (50 mL), n-BuLi (1.6 M n-hexane solution, 1.25 mL, 2.0 mmol) was added dropwise via a syringe at −78° C. Then the resulting yellow solution was stirred for further 2 h at room temperature. After cooling the mixture to −78° C., cyclic sulfate 20 (0.78 g, 2.0 mmol) in THF (30 mL) was added over 10 min. The resulting brown solution was warmed to room temperature and stirred for 4 h. After cooling to −78° C., n-BuLi (1.6 M solution in n-hexane, 1.25 mL, 2.0 mmol) was added and the reaction mixture was stirred for an additional 20 h at room temperature. Then $BH_3$-THF complex (1 M solution in THF, 3.0 mL, 3.0 mmol) was added at 0° C. After stirring overnight, the solvents were removed under reduced pressure. Water (30 mL) was added to the residue and the aqueous solution extracted with $CH_2Cl_2$ (3×40 mL). The combined organic layers were dried ($Na_2SO_4$) and concentrated to afford the crude phospholane-borane as a colorless syrup. Purification was performed by flash chromatography (hexanes/AcOEt= 9:1) to give the 21-borane adduct as a white solid (767 mg, 92%). $^1$H NMR (CDCl$_3$): δ7.87–7.82 (m, 2H, aromatic), 7.31–7.16 (m, 3H, aromatic), 4.56–4.42 (m, 4H), 4.02–3.90 (m, 2H), 2.78–2.72 (m, 2H), 1.22–1.16 (m, 3H), 0.85–0.79 (m, 3H), 1.23–0 (broad, 3H, BH$_3$). $^{13}$C NMR (CDCl$_3$): δ138.0, 137.6, 134.5, 134.4, 131.1, 128.5–126.4, 83.7, 83.4, 72.6, 72.3, 36.2, 35.8, 9.2, 9.1. $^{31}$P NMR (CDCl$_3$): δ37.1, b, ppm. The 21-borane adduct was dissolved in 20 mL of toluene and 2 equivalent of DABCO was added. The resulting mixture was heated at 50° C. for 8 h. After removal of the solvent, the residue was passed through a plug of silica gel eluted with hexane/ethyl acetate (9:1) to afford phosphine 21 as a colorless oil. $^{31}$P NMR (CDCl$_3$): δ3.8 ppm.

EXAMPLE 4

Phosphine 10

To a stirred solution of 1,2-bis(phosphino)benzene (1.24 g, 8.72 mmol) in THF (200 mL), n-BuLi (1.6 M n-hexane solution, 10.9 mL, 17.4 mmol) was added dropwise via a syringe at −78° C. Then the resulting yellow solution was stirred for further 2 h at room temperature. After cooling the mixture to −78° C., cyclic sulfate 9 (4.39 g, 17.4 mmol) in THF (50 mL) was added over 10 min. The resulting yellow solution was warmed to room temperature and stirred for 4 h. After cooling to −78° C. n-BuLi (1.6 M solution in n-hexane, 11.0 mL, 17.5 mmol) was added, and the reaction mixture was stirred for additional 20 h at room temperature. After removal of the solvent under reduced pressure, the residue was dissolved in 50 mL of ethyl ether, and 50 mL of brine was added. The aqueous layer was then washed with 3×40 mL ethyl ether. The combined organic layers were dried over $Na_2SO_4$ and concentrated to afford a colorless crystal. This crystal was further recrystallized from ether/methanol. $^1$H NMR (CDCl$_3$): δ7.38–7.33 (m, 4H, aromatic), 4.46–4.36 (m, 4H), 2.89–2.82 (m, 2H), 2.56–2.51 (m, 2H), 1.47 (s, 6H), 1.42 (s, 6H), 1.33–1.28 (m, 6H), 0.73–0.69 (m, 6H); $^{13}$C NMR (CDCl$_3$): δ140.53, 130.59, 129.00, 117.44, 81.41, 80.51 (t, $J_{PC}$=6.5 Hz), 27.34, 27.30, 25.05 (t, $J_{PC}$=10.3 Hz), 24.20, 13.74 (t, $J_{PC}$=19.6 Hz), 12.15; $^{31}$P NMR (CDCl$_3$): δ45.1 ppm. HRMS calcd for $C_{24}H_{37}O_4P_2$ (MH$^+$) 451.2167; found 451.2164.

EXAMPLE 5

Phosphine 2

Phosphine 10 obtained above was disolved in 100 mL of methanol and 2 mL of water. 0.1 mL of methanesufonic acid was added and the resulting mixturing was refluxing for 10 h. After removal of the solvent the residue was passed through a short plug of silica gel eluted with ethyl acetate/methanol (95:5) to give compound 2 as a white solid.$^1$H NMR (CD$_3$OD): δ8.42–8.07 (m, 2H, aromatic), 7.72–7.69 (m, 2H, aromatic), 4.24–4.17 (m, 4H), 3.31–3.28 (m, 2H), 3.16–3.13 (m, 2H), 1.37–1.30 (m, 6H), 0.94–0.88 (m, 6H); $^{13}$C NMR (CD$_3$OD): δ136.6 (t, $J_{PC}$=3.4 Hz), 133.7, 133.6, 80.2, 80.0, 37.3, 35.4 (d, $J_{PC}$=10.0 Hz), 11.6 (d, $J_{PC}$=6.5 Hz), 10.8. $^{31}$P NMR (CD$_3$OD): δ11.9 (broad) ppm. HRMS calcd for $C_{18}H_{29}O_4P_2$ (MH$^+$) 371.1541; found 371.1523.

EXAMPLE 6

Phosphines 14 and 3

Phosphine 14 was prepared using the similar procedure for 10 and recrystallized from ethyl ether/methanol as a colorless crystal. $^1$H NMR (CDCl$_3$): δ7.41–7.32 (m, 4H, aromatic), 4.50–4.37 (m, 4H), 2.62–2.61 (m, 2H), 2.22–2.20 (m, 2H), 2.19–2.17 (m, 2H), 1.50–1.44 (m, 2H), 1.47 (s, 6H), 1.32–1.30 (m, 2H), 0.99–0.95 (m, 6H), 0.88–0.86 (m, 2H), 0.79–0.75 (m, 6H); $^{13}$C NMR (CDCl$_3$): δ141.3, 131.1, 129.2, 117.1, 82.3, 81.4 (t,=6.1 Hz), 33.0, 32.8 (t,=9.6), 27.4, 27.3, 21.4, 21.1 (t,=14.2), 14.6, 13.1 (t,=5.1 Hz).; $^{31}$P NMR (CDCl$_3$): δ34.5 ppm. Catalytic acid hydrolysis give phosphine 3.

EXAMPLE 7

General Procedure for Asymmetric Hydrogenation

To a solution of [Rh(COD)$_2$]X (X=counterion) (5.0 mg, 0.012 mmol) in THF (10 mL) in a glovebox was added chiral ligand (0.15 mL of 0.1 M solution in toluene, 0.015 mmol). After stirring the mixture for 30 min, the dehydroamino acid (1.2 mmol) was added. The hydrogenation was performed at room temperature under hydrogen for 24 h. The reaction mixture was treated with $CH_2N_2$, then concentrated in Vacuo. The residue was passed through a short silica gel column to remove the catalyst. The enantiomeric excesses were measured by GC using a Chirasil-VAL III FSOT column. The absolute configuration of products was determined by comparing the observed rotation with the reported value. All reactions went in quantitative yield with on by-products found by GC.

EXAMPLE 8

General Procedure for the Bavlis-Hillman Reaction

The mixture of 4-pyridinecarbonaldehyde (1 mmol) and 1 mL of methyl acrylate was degassed three times by a freeze-thaw method, and then the resulting solution was transferred into another Schlenk tube containing 10% catalyst. The solution was stirred at room temperature for some time and the methyl acrylate was removed under vaccm. The residue was purified by a flash chromatograph eluted with hexanes/ethyl acetate (1:2). The enantiomeric excess was measured by capillary GC.

Asymmeric Baylis-Hillman reaction

TABLE 1

Catalytic Baylis-Hillman Reaction

| Run | Catalyst | Reaction Time | Yield (%) | % ee |
|---|---|---|---|---|
| 1 | 21 | 70 h | 29 | 19 |
| 2 | 1 | 9 h | 83 | 17 |
| 3 | 18 | 31 h | 56 | 18 |

The reaction was accelerated significantly when hydroxyl phosphine was used as catalyst. For example, the reaction takes 70 h and gives lower yield (29%) with benzyl protected hydroxyl phospholane 21 as catalyst, while the same reaction proceeds in 9 h and offers high yield (83%) with hydroxyl phospholane 1. This demonstrates the importance of the hydroxyl group in the catalytic system.

Hydrogenation of Dehydroamino Acids

TABLE 2

Asymmetric Hydrogenation of Dehydroamino Acid Derivatives[a]

| Run | Substrate | Ligand | % ee[b] | Ligand | % ee |
|---|---|---|---|---|---|
| 1 | R = H, R' = H | 2 | >99[c] | 3 | >99 |
| 2 | R = H, R' = CH$_3$ | 2 | 98.3 | 3 | 99 |
| 3 | R = Ph, R' = H | 2 | >99[c] | 3 | >99 |
| 4 | R = Ph, R' = CH$_3$ | 2 | >99 | 3 | >99 |
| 5 | R = p-F—Ph , R' = H | 2 | 98.5[c] | 3 | >99 |
| 6 | R = p-F—Ph , R' = CH$_3$ | 2 | 98.4 | 3 | >99 |
| 7 | R = p-MeO—Ph , R1 = H | 2 | 98.1[c,d] | 3 | 99 |
| 8 | R = p-MeO—Ph , R' = CH$_3$ | 2 | 98.3[d] | 3 | >99 |
| 9 | R = 2-thienyl, R' = H | 2 | >99[c] | 3 | >99 |
| 10 | R = 2-thienyl, R' = CH$_3$ | 2 | >99 | 3 | >99 |
| 11 | R = m-Br—Ph , R' = H |  |  | 3 | 99 |
| 12 | R = m-Br—Ph , R' = CH$_3$ |  |  | 3 | >99 |
| 13 | R = o-Cl—Ph , R' = H |  |  | 3 | 98 |
| 14 | R = o-Cl—Ph , R' = CH$_3$ |  |  | 3 | 98 |
| 15 | R = 2-naphthyl, R' = H |  |  | 3 | >99 |
| 16 | R = 2-naphthyl, R' = CH$_3$ |  |  | 3 | >99 |
| 17 | R = Ph, R' = H, benzonate |  |  | 3 | >99 |
| 18 | R = Ph, R' = CH$_3$, benzonate |  |  | 3 | >99 |

[a]The reaction was carried out at rt under 3 atm (45 psi) of H$_2$ for 12 h in 3 mL of methanol with 100% conversion [substrate (0.5 mmol):[Rh(COD)$_2$]PF$_6$:ligand 4 = 1:0.01:0.011].
[b]The S absolute configurations were determined by comparing optical rotations with reported values. The % ee was determined by GC using a Chiral-VAL III FSOT column.
[c]Determined on the corresponding methyl ester.
[d]The % ee was determined by HPLC using a Chiral OJ column.

Catalytic Asymmetric Hydrogenation of Itaconic Acid Derivatives

TABLE 3

Asymmetric Hydrogenation of Itaconic Acid Derivatives

| Run | Substrate | Ligand | % ee | Ligand | % ee[a] |
|---|---|---|---|---|---|
| 1 | R = H | 2 | 95.7 | 3 | >99 |
| 2 | R = CH$_3$ | 2 | 97.5 | 3 | >99 |
| 3 | R = CH$_3$ |  |  | 3[b] | >99 |

[a]Determined by GC using a gamma-225 column at 100° C.
[b]Run in 3:97 MeOH/H$_2$O instead of neat MeOH. Various MeOH/H$_2$O ratios gave comparable results.

Catalytic Asymmetric Hydrogenation of Enamides

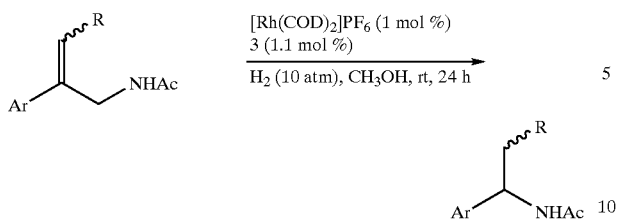

TABLE 4

Asymmetric Hydrogenation of Enamides

| Run | Substrate | Ligand | % ee |
|---|---|---|---|
| 1 | Ar = Ph, R = H | 3 | 95.8 |
| 2 | Ar = p-MeO—Ph, R = H | 3 | 95.3 |
| 3 | Ar = p-F$_3$C—Ph, R = H | 3 | 98.1 |
| 4 | Ar = p-Cy—Ph, R = H | 3 | 97.7 |

EXAMPLE 9

Asymmetric Hydrogenation Using Ligand 24

The synthetic route to ligand 24 is shown in Scheme 1. From an inexpensive and commercially available starting material, D-mannitol, the important intermediate 1,4-diol cyclic sulfate 9 was prepared according to the reported method. See Li, W. et al., Tetrahedron Letter (1999) 40, 6701; Li, W. et al., J. Org. Chem. (2000) 65, 3489; Yan, Y. -Y et al., Org. Letter (2000) 2, 199; Yan, Y. -Y et al., J. Org. Chem (2000) 65, 900; Merver, Y. L. et al., Heterocycles (1987) 25, 541; Allevi, P. et al., Tetrahedron: Asymmetry (1994) 5, 927; Gao, Y. et al., J. Am. Chem. Soc. (1988) 110, 7538; Kim, B. M. et al., Tetrahedron Letter (1989) 30, 655; Holz, J. et al., J. Org. Chem (1998) 63, 8031; Carmichael, D. et al., Chem. Commun. (1999) 261. The 1,1'-bis(phosphino) ferrocene was prepared from ferrocene through a two-step procedure. See Burk, M. J. et al., Tetrahedron Letter (1994) 35, 9363. Nucleophilic attack of 9 with 1,1'-bis(phosphino) ferrocene in the presence of n-BuLi affords ligand 24. $^1$H NMR (360 MHz, C$_6$D$_6$) δ4.55–4.50 (m, 2H), 4.34–4.29 (m, 2H), 4.14–4.12 (m, 4H), 4.05 (m, 2H), 3.72 (m, 2H), 2.38–2.30 (m, 4H), 1.51–1.44 (m, 18H), 0.80–0.76 (m, 6H); $^{13}$C NMR (400 MHz, C$_6$D$_6$) δ117.6 (s), 82.3–82.2 (m), 77.4 (d, J$_{CP}$=37.3 Hz), 75.2 (d, J$_{CP}$=25.3 Hz), 72.3 (d, J$_{CP}$=44.8 Hz), 70.3–70.4 (m), 27.7 (s), 27.6 (s), 26.6–26.4 (m), 14.3 (s), 14.0 (s), 11.2 (s); $^{31}$P NMR (360 MHz, C$_6$D$_6$) δ39.3; mp 152–154° C.; HRMS: m/z calcd for C$_{28}$H$_{40}$O$_4$P$_2$Fe (M$^+$) 559.1829, found 559.1846. The new ligand can be easily purified by running column chromatography in dry-box to give an orange solid in an acceptable yield.

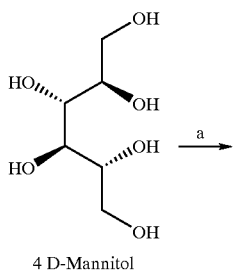

4 D-Mannitol

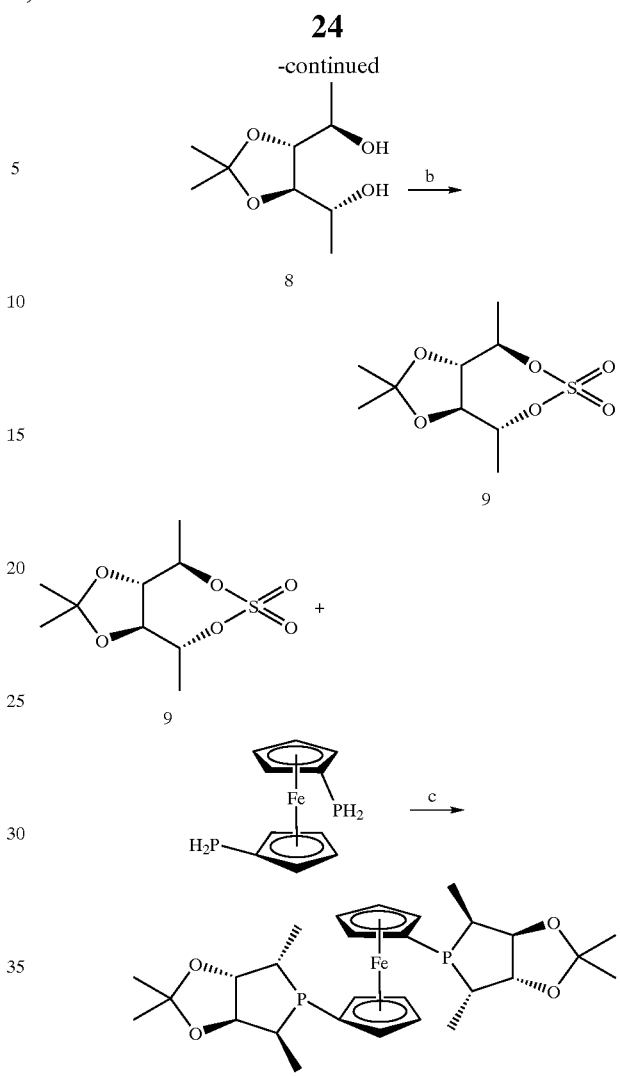

24 f-ketalPhos (a) See Merver, Y. L. et al., Heterocycles (1987) 25, 541; Allevi, P. et al., Tetrahedron: Asymmetry (1994) 5, 927;
(b) (i) SOCl$_2$, Et$_3$N, CH$_2$Cl$_2$, 0° C., (ii) NaI O$_4$, RuCl$_3$.xH$_2$O, 0° C. See Gao, Y. et al., J. Am. Chem. Soc. (1988) 110, 7538; Kim, B. M. et al., Tetrahedron Letter (1989) 30, 655;
(c) (i) 1,1'-bis(phosphino)ferrocene, n-BuLi, THF, -78° C.–0° C., 2 h, (ii) 8, THF, -78° C.–0° C., 4 h, (iii) n-BuLi, THF, -78° C.–0° C., 6 h, then reflexing for 30 min.

The Rh(I)-catalyzed hydrogenation of dehydroamino acids and their ester derivatives was performed with ligand 24. The catalytic complex was prepared in situ by mixing Rh(COD)$_2$ PF$_6$ and 24 in solvent. The commercially available α-(N-acetamido)acrylate 25a was chosen to screen the reaction conditions. The results are shown in Table 5. Excellent enantioselectivity (over 99% ee) was observed for this reaction. This result is superior to those obtained with ligand 22 (83% ee) and ligand 23 (94% ee). No solvent effect was found. This system works very well in both polar and non-polar solvents (entries 5–8). In decreasing the H$_2$ pressure from 45 psi to 20 psi and reducing the reaction time to 30 min, no deterioration was observed with respect to either conversion or enantioselectivity. This indicates that this catalytic system is not only highly enantioselective but also highly efficient.

TABLE 5

Rh(I)-24 Catalyzed Asymmetric Hydrogenation of
α-(N-acetamido)acrylate 25a[a]

$$\underset{25}{\underset{NHAc}{\overset{COOCH_3}{\diagup}}} + H_2 \xrightarrow[rt]{[Rh(COD)_2]PF_6 \ (1\ mol\ \%)\ +\ 24\ (1.1\ mol\ \%)} \underset{(S)-26a^b}{\underset{NHAc}{\overset{COOCH_3}{\diagup}}}$$

| Entry | Ligand | Solvent | Pressure of H₂ (psi) | Time (h) | ee (%)[f] |
|---|---|---|---|---|---|
| 1[c] | 22a[e] | MeOH | 60 | ≥6 | 64 |
| 2[c] | 22b[e] | MeOH | 60 | ≥6 | 83 |
| 3[d] | 23a[e] | MeOH | 60 | 18 | 69 |
| 4[d] | 23b[e] | MeOH | 60 | 18 | 94 |
| 5 | 6 | MeOH | 45 | 3 | >99 |
| 6 | 6 | DCM | 45 | 3 | >99 |
| 7 | 6 | THF | 45 | 3 | >99 |
| 8 | 6 | Toluene | 45 | 3 | >99 |
| 9 | 6 | MeOH | 45 | 0.5 | >99 |
| 10 | 6 | MeOH | 20 | 0.5 | >99 |

[a]Hydrogenation Conditions: The reaction was carried at rt. In situ catalyst, [Rh(COD)₂PF₆] (1.0 mol %) and 24 (1.1 mol %), was stirred for 15 min prior to introduction of substrate and H₂. The reaction went with 100% conversion.
[b]The S absolute configuration was assigned by comparison of optical rotation with reported data.
[c]See Berens, U. et al., Angew. Chem. Int. (2000) 39, 1981.
[d]See Marinetti, A. et al., Synlett (1999) 12, 1975.
[e]Ligand 22a R = Me; 22b R = Et; 23a R = Me; 23b R = i-Pr.
[f]Enantiomeric excesses were determined by chiral GC using a Chirasil-VAL III FSOT column.

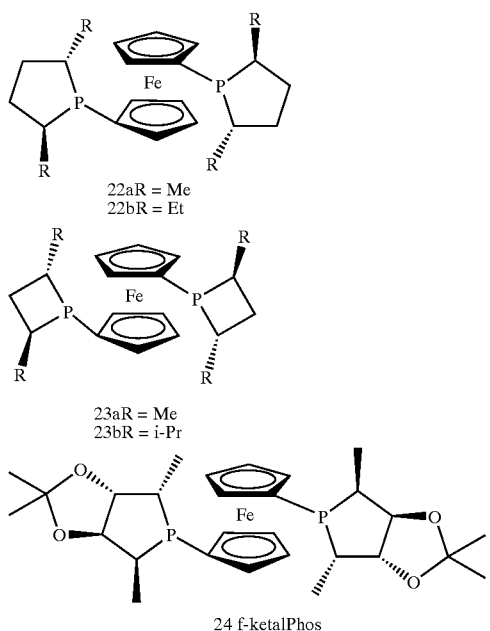

22aR = Me
22bR = Et

23aR = Me
23bR = i-Pr 24 f-ketalPhos

Table 6 summarizes the results of Rh(I)-24 complex catalyzed hydrogenation of different dehydroamino acids and some ester derivatives 25. For most tri-substituted dehydroamino acids and esters, high selectivity was achieved (95–99% ee). One exception was the substrate in which R=p-MeO-phenyl (entry 9), only 88.3% ee was obtained, and the reaction was not complete after 3 h, which is normally enough for most substrates. Tetra-substituted dehydroamino acid was also explored (entry 16), but the ee value (88.8%) was a little lower than those for the tri-substituted substrates. Irregardless, the overall enantioselectivities for the Rh(I)-24 catalyzed hydrogenation of dehydroamino acid derivatives were quite good and comparable with those attained with the best chiral bisphosphine systems, especially when considering that among the current C₂-symmetric ferrocenyl-bisphosphine ligands, these results are among the best reported to date. See Marinetti, A. et al., Synlett (1999) 12, 1975; Berens, U. et al., Angew. Chem. Int. (2000) 39, 1981; Sawamura, M. et al., J. Am. Chem. Soc. (1995) 117, 9602; Kang, J. et al., Tetrahedron Letter (1998) 39, 5523; Perea, J. J. A. et al., Tetrahedron Letter (1998) 39, 8073; Perea, J. J. A. et al., Tetrahedron: Asymmetry (1999) 10, 375; Nettekoven, U. et al., J. Org. Chem. (1999) 64, 3996.

TABLE 6

Rh(I)-24 Catalyzed Asymmetric Hydrogenation of
Dehydroamino Acid Derivatives[a]

$$\underset{25a}{\underset{NHAc}{\overset{R}{\diagup}}\overset{COOR'}{\diagdown}} + H_2 \xrightarrow[CH_3OH,\ rt]{[Rh(COD)_2]PF_6\ (1\ mol\ \%)\ +\ 24\ (1.1\ mol\ \%)} \underset{(S)-26^b}{\underset{NHAc}{\overset{R}{\diagup}}\overset{COOR}{\diagdown}}$$

| Entry | Substrate | ee (%)[c] |
|---|---|---|
| 1 | R = H, R' = H | >99[d] |
| 2 | R = H, R' = CH₃ | >99 |
| 3 | R = i-pr, R' = H | >99[d] |
| 4 | R = Ph, R' = H | 94[d] |
| 5 | R = Ph, R' = CH₃ | 96 |
| 6 | R = p-F—Ph, R' = H | 95[d] |
| 7 | R = p-F—Ph, R' = CH₃ | 95 |
| 8 | R = p-MeO—Ph, R' = H | |
| 9 | R = p-MeO—Ph, R' = CH₃ | 88[e,f] |
| 10 | R = o-Cl—Ph, R' = H | |
| 11 | R = o-Cl—Ph, R' = CH₃ | 97 |
| 12 | R = m-Br—Ph, R' = H | 98[d] |
| 13 | R = m-Br—Ph, R' = CH₃ | 97 |
| 14 | R = 2-naphthyl, R' = H | 98[d] |
| 15 | R = 2-naphthyl, R' = CH₃ | 97 |
| 16 | ![structure with COOCH₃ and NHAc] | 89 |

[a]Hydrogenation Condition: The reaction was carried at rt under 45 psi of H2 for 3–6 h. In situ catalyst, [Rh(COD)₂PF₆] (1.0 mol %) and 6 (1.1 mol %), was stirred for 15 min prior to introduction of substrate and H₂. The reaction went with 100% conversion.
[b]The S absolute configuration was assigned by comparison of optical rotation with reported data.

TABLE 6-continued

Rh(I)-24 Catalyzed Asymmetric Hydrogenation of Dehydroamino Acid Derivatives[a]

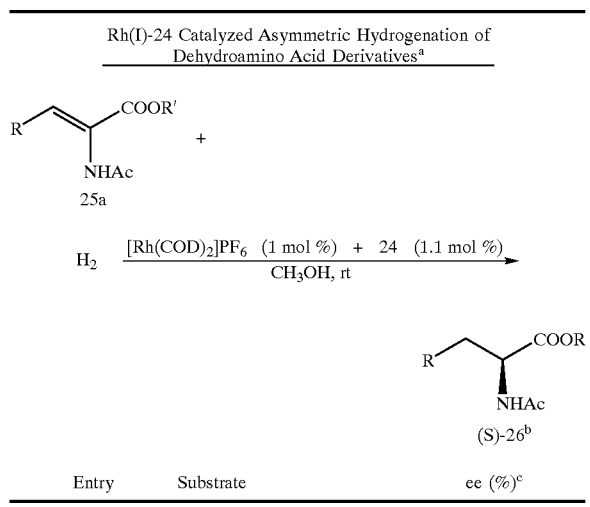

| Entry | Substrate | ee (%)[c] |
|---|---|---|

[c]Enantiomeric excesses were determined by chiral GC using a Chirasil-VAL III FSOT column.
[d]Determined on the corresponding methyl ester.
[e]The % ee was determined by HPLC using a Daicel Chiralcel OJ column.
[f]The reaction was not complete as indicated by TLC after 3 h.

Hydrogenation of itaconic acid derivatives was also preliminarily explored with the same catalytic system as above. The reaction was carried at rt under 80 psi of H2 for 12 h. In situ catalyst, [Rh(COD)$_2$ PF$_6$] (1.0 mol %) and 24 (1.1 mol %), was stirred for 15 min prior to introduction of substrate and H$_2$. The reaction went with 100% conversion. The R absolute configuration was assigned by comparison of optical rotation with reported data. Enantiomeric excesses were determined on the corresponding dimethyl ester by chiral GC using a gamma-225 column. Excellent results, 99% ee and 96% ee were achieved for itaconic acid 27a and its derivative 27b, respectively.

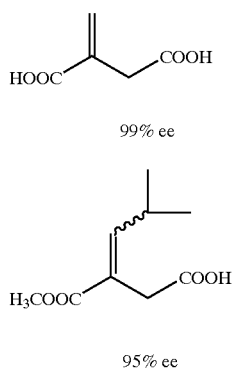

Example 10

Asymmetric Allylic Alkylation Using Ligands Me-f-KetalPhos (24), Et-f-KetalPhos (28) and Me-KetalPhos (10)

Palladium compounds with chiral ligands f-KetalPhos and KetalPhos are effective catalysts for asymmetric allylic alkylation of allylic esters. Table 7 lists some experimental results obtained in this reaction. [Pd(Cl)(C$_3$H$_5$)]$_2$ was used as the catalytic precursor, KOAc and BSA were used in the reaction. The reactions were run in either CH$_2$Cl$_2$ or THF.

With chiral ligand 24, up to 91% ee was obtained. Modification of Me-f-KetalPhos (24) to Et-f-KetalPhos (28) lead to a higher ee (94%). In CH$_2$Cl$_2$, Up to 99% ee was achieved with a palladium catalyst bearing the Me-ketalPhos (10) ligand. The yields of these reactions are all over 95% under the reaction conditions.

TABLE 7

Pd.-Catalyzed Asymmetric Allylic Alkylation

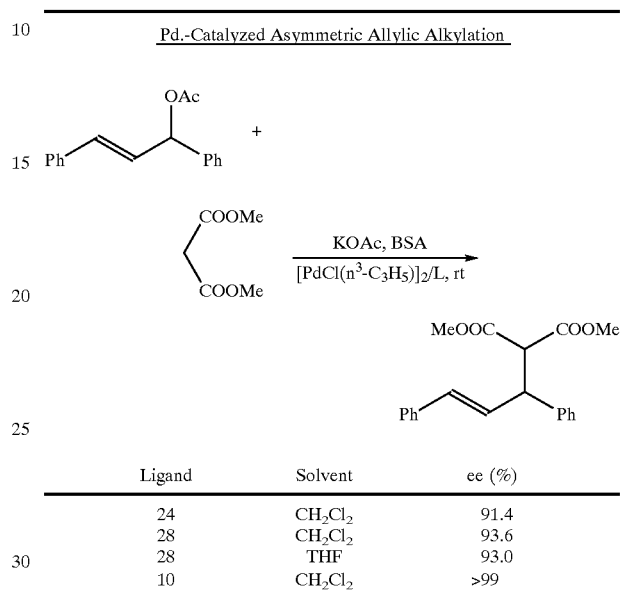

| Ligand | Solvent | ee (%) |
|---|---|---|
| 24 | CH$_2$Cl$_2$ | 91.4 |
| 28 | CH$_2$Cl$_2$ | 93.6 |
| 28 | THF | 93.0 |
| 10 | CH$_2$Cl$_2$ | >99 |

The foregoing written description relates to various embodiments of the present invention. Numerous changes and modifications may be made therein without departing from the spirit and scope of the invention as defined in the following claims.

What is claimed is:

1. A catalyst comprising a chiral compound in the form of a complex with a transition metal wherein said compound is represented by the formula B, B', D, D' or the corresponding enantiomers:

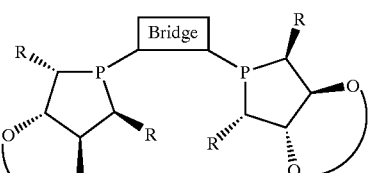

B

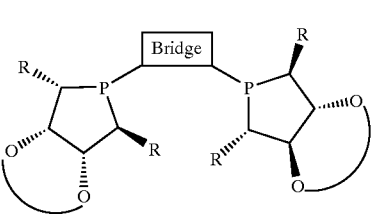

B'

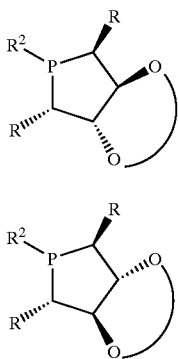

wherein:
a) R and $R^2$ are independently aryl, alkyl, alkyl aryl, aryl alkyl, or chiral oxazolino which may be substituted with carboxylic acid, alkoxy, hydroxy, alkylthio, thiol or dialkylamino groups;
b) the ring component

represents a protected diol, a crown ether linkage, —O-alkyl-O— wherein the alkyl group is linked to a polymer, or —O—(CH$_2$CH$_2$—O)$_n$— wherein n is an integer ranging from 1 to 8 and the methylene groups are optionally substituted by C1–C8 alkyl;
c) in formulas B and B', the Bridge may be:
- —(CH$_2$)$_n$— where n is an integer ranging from 1 to 8;
- —(CH$_2$)$_n$X(CH$_2$)$_m$ — wherein n and m are each integers, the same or different, ranging from 1 to 8, and X is O, S, NR$^4$, PR$^4$, AsR$^4$, SbR$^4$, divalent aryl, divalent fused aryl, divalent 5-membered ring heterocyclic group, or divalent fused heterocyclic group, wherein R$^4$ is aryl, alkyl, substituted aryl, or substituted alkyl; or
- 1,2-divalent phenyl, 2,2'-divalent 1,1'biphenyl or 2,2'-divalent 1,2'-binapthyl or ferrocene, each of which may be substituted with aryl, C1–C8 alkyl, F, Cl, Br, I, COOR$^5$, SO$_3$R$^5$, PO$_3$R$^5$$_2$, OR$^5$, SR$^5$, NR$^5$$_2$, PR$^5$$_2$, AsR$^5$$_2$, or SbR$^5$$_2$;
wherein the substitution on 1,2-divalent phenyl, the ferrocene or biaryl bridge can be independently halogen, alkyl, alkoxyl, aryl, aryloxy, nitro, amino, vinyl, substituted vinyl, alkynyl, or sulfonic acids; and
R$^5$ is C1–C8 alkyl, C1–C8 fluoroalkyl, or C1–C8 perfluoroalkyl, aryl; substituted aryl; arylalkyl; ring-substituted arylalkyl; or —CR$^3$$_2$(CR$^3$$_2$)$_q$X(CR$^3$$_2$)$_p$R$^1$ wherein q and p are integers, the same or different, ranging from 1 to 8; R$^3$ is aryl, alkyl, substituted aryl, or substituted alkyl; and X is as defined above.

2. A catalyst according to claim 1, wherein the transition metal is rhodium, iridium, ruthenium, nickel, or palladium.

3. A catalyst according to claim 2, wherein said transition metal complex is formed from a compound selected from the group consisting of: Pd$_2$(DBA)$_3$, Pd(OAc)$_2$; [Rh(COD) Cl]$_2$, [Rh(COD)$_2$]X, Rh(acac)(CO)$_2$; RuCl$_2$(COD), Ru(COD)(methylallyl)$_2$, Ru(Ar)Cl$_2$, wherein Ar is an aryl group, unsubstituted or substituted with an alkyl group; [Ir(COD)Cl]$_2$, [Ir(COD)$_2$]X; and Ni(allyl)X; wherein X is a counterion.

4. A catalyst according to claim 3, wherein X is selected from the group consisting of: Fl$^-$, Cl$^-$, Br$^-$, I$^-$, BF$_4^-$, ClO$_4^-$, SbF$_6^-$, CF$_3$SO$_3^-$, and PF$_6^-$.

5. A catalyst according to claim 4 wherein X is PF$_6^-$.

6. A catalyst according to claim 2 wherein the transition metal is Ru or Rh.

7. A catalyst according to claim 6 wherein the transition metal is Ru or Rh.

8. A catalyst according to claim 1, wherein said transition metal complex is formed from a compound selected from the group consisting of: Ru(RCOO)$_2$(diphosphine), RuX$_2$(diphosphine), Ru(methylallyl)$_2$(diphosphine), Ru(aryl group)X$_2$(diphosphine), Rh(RCOO)$_2$(diphosphine), RhX$_2$(diphosphine), Rh(methylallyl)$_2$ diphosphine, or Rh(aryl group)X$_2$ (diphosphine) and X is halogen.

9. A catalyst according to claim 1, wherein said chiral compound is represented by the following formula:

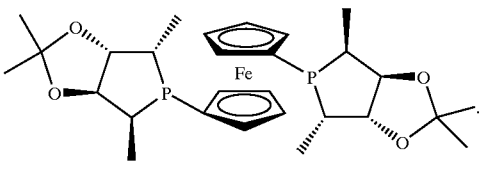

24 f-ketalPhos

10. A catalyst comprising a transition metal complex of a compound of the following formula or its enantiomer:

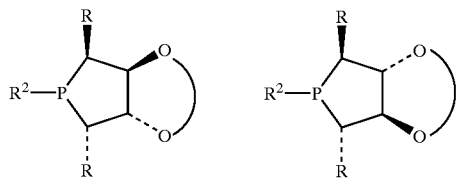

wherein

A) R is C$_1$–C$_8$ alkyl, C$_1$–C$_8$ alkyl aryl, aryl C$_1$–C$_8$ alkyl, aryl, each of which may be substituted with carboxylic acid, alkoxy, hydroxy, alkylthio, thiol, dialkylamino, diphenylphosphino or chiral oxazoline; and B) the ring components

represents a protected diol, a crown ether linkage, —O—C$_1$–C$_8$ alkyl-O— wherein the alkyl group is linked to a polymer, —O—(CH$_2$CH$_2$—O—wherein n is an integer ranging from 1 to 8 and the methylene groups are optionally substituted by C$_1$–C$_8$ alkyl, or O-W-O, where W is BR$^9$, POR$^9$, PO (OR$^9$), SO$_2$, C), or Si(R$^9$)$_2$;

where R$^9$ C$_1$–C$_8$ alkyl, aryl, C$_1$–C$_8$ alkyl aryl, or aryl C$_1$–C$_8$ alkyl, alkoxy, hydroxy, alkylthio, thio, alkylamino, dialkylamino; and C)R$^2$ is either R, H, phenyl or a symmetrical bidentate structure having the formula

wherein

is i) —(CH$_2$)$_n$—where n is an integer from 1 to 8; or
ii) —(CH$_2$)$_n$X(CH$_2$)$_m$—where n and m are the same or different integers from 1 to 8, and X is O, S, NR$^4$, PR$^4$, AsR$^4$, SbR$^4$, divalent aryl, divalent fused aryl, divalent 5-membered heterocyclic ring, or divalent fused heterocyclic ring, where R$^4$ is C$_1$–C$_8$ alkyl, aryl, substituted aryl, or substituted alkyl; or
iii) 1,2-divalent phenyl, 2,2'-divalent 1,1'biphenyl, 2,2'-divalent, 1,1' binapthyl, or ferrocene, each of which may be substituted independently with C$_1$–C$_8$ alkyl or aryl, F, Cl, Br, I, COOR$^5$, SO$_3$R$^5$, PO$_3$R$^5{}_2$, OR$^5$, SR$^5$, NR$^5{}_2$, PR$^5{}_2$, AsR$^5{}_2$, SbR$^5{}_2$, nitro, vinyl, substituted vinyl, alkynyl wherein R$^5$ is H, C$_1$–C$_8$ alkyl, substituted C$_1$–C$_8$ alkyl, C$_1$–C$_8$ fluoroalkyl, C$_1$–C$_8$ perfluoroalkyl, aryl or substituted aryl; and
wherein Z is a compound selected from the group of compounds having the following formulas and their corresponding enantiomers:

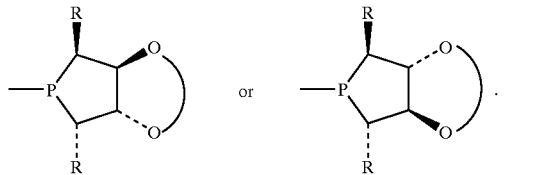

11. A catalyst according to claim 10, wherein the transition metal is rhodium, iridium, ruthenium, nickel, or palladium.

12. A catalyst according to claim 10, wherein said transition metal complex is formed from a compound selected from the group consisting of:

Pd$_2$(DBA)$_3$, Pd(OAc)$_2$; [Rh(COD)Cl]$_2$, [Rh(COD)$_2$]X, Rh(acac)(CO)$_2$; RuCl$_2$(COD), Ru(COD)(methylallyl)$_2$, Ru(Ar)Cl$_2$, wherein Ar is an aryl group, unsubstituted or substituted with an alkyl group; [Ir(COD)Cl]$_2$, [Ir(COD)$_2$]X; and Ni(allyl)X; wherein X is a counterion selected from the group consisting of: Fl$^-$, Cl$^-$, Br$^-$, I$^-$, BF$_4{}^-$, ClO$_4{}^-$, SbF$_6{}^-$, CF$_3$SO$_3{}^-$, and PF$_6{}^-$.

13. A catalyst according to claim 10, wherein said transition metal complex is formed from a compound selected from the group consisting of:

Ru(RCOO)$_2$(diphosphine), RuX$_2$(diphosphine), Ru(methylallyl)$_2$(diphosphine), Ru(aryl group)X$_2$ (diphosphine), Rh(RCOO)$_2$(diphosphine), RhX$_2$ (diphosphine), Rh(methylallyl)$_2$ diphosphine, or Rh(aryl group)X$_2$ (diphosphine) and X is halogen.

14. A catalyst according to claim 10, wherein said compound is represented by the following formula:

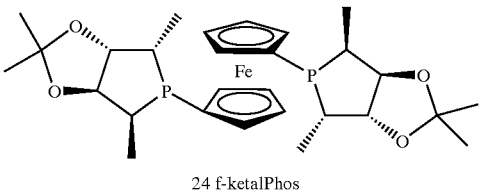

24 f-ketalPhos wherein said transition metal is rhodium, iridium, ruthenium, nickel or palladium; and wherein said transition metal complex is formed from: Pd$_2$(DBA)$_3$, Pd(OAc)$_2$; [Rh(COD)Cl]$_2$, [Rh(COD)$_2$]X, Rh(acac)(CO)$_2$; RuCl$_2$(COD), Ru(COD)(methylallyl)$_2$ Ru(Ar)Cl$_2$ wherein Ar is an aryl group unsubstituted or substituted with an alkyl group, [Ir(COD)Cl$_2$], [Ir(COD)$_2$]X or Ni(allyl)X, wherein X is a counterion selected from the group consisting of: Fl$^-$, Cr$^-$, Br$^-$, I$^-$, BF$_4{}^-$, ClO$_4{}^-$, SbF$_6{}^-$, CF$_3{}^-$SO$_3{}^-$, and PF$_6{}^-$; or Ru(RCOO)$_2$(diphosphine) RuX$_2$(diphosphine), Ru(methylallyl)$_2$(diphosphine), Ru(aryl group)X$_2$ (diphosphine), Rh(RCOO)$_2$(diphosphine) RhX$_4$diphosphine), Rh(methylallyl)$_2$ diphosphine or Rh(aryl group)X$_2$ (diphosphine), wherein X is halogen.

* * * * *

UNITED STATES PATENT AND TRADEMARK OFFICE
CERTIFICATE OF CORRECTION

PATENT NO. : 6,727,377 B2  Page 1 of 1
APPLICATION NO. : 09/992551
DATED : April 27, 2004
INVENTOR(S) : Xumu Zhang It is certified that error appears in the above-identified patent and that said Letters Patent is hereby corrected as shown below:

Column 28
Claim 1, in formula B' structure, phosphorous containing five-member ring on the left side of the bridge, going clockwise from phosphorous atom, the first R is up (solid line), the first O is down (dotted line), the second O should be up (solid line) instead of down (dotted line) as it appears in the patent, the second R is down (dotted line).

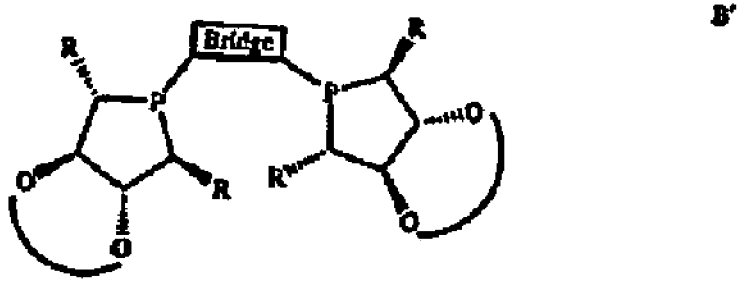

Column 30
Line 12, Claim 7, should read: --A catalyst according to claim 6 wherein the transition metal is Rh.--

Column 30
Line 61, Claim 10, "C)" should read --CO--
Line 62, "where $R^9$ $C_1$-$C_8$" should read --where $R^9$ is $C_1$-$C_8$ --

Signed and Sealed this

Twenty-fourth Day of April, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,727,377 B2 | Page 1 of 1 |
| APPLICATION NO. | : 09/992551 | |
| DATED | : April 27, 2004 | |
| INVENTOR(S) | : Xumu Zhang | |

It is certified that error appears in the above-identified patent and that said Letters Patent is hereby corrected as shown below:

Column 1,
Line 11, after "...Aug.21, 1998." please add the following heading and paragraph from Line 12 and following:

--FEDERALLY SPONSORED RESEARCH AND DEVELOPMENT

> This invention was made with support from the Government under Office of Naval Research Contract No. N00014-96-1-0733 and the National Science Foundation Grant No. CHE9712201. The Government has certain rights in the invention.--

Signed and Sealed this

Twenty-sixth Day of February, 2008

JON W. DUDAS
*Director of the United States Patent and Trademark Office*

UNITED STATES PATENT AND TRADEMARK OFFICE
CERTIFICATE OF CORRECTION

PATENT NO. : 6,727,377 B2  Page 1 of 1
APPLICATION NO. : 09/992551
DATED : April 27, 2004
INVENTOR(S) : Xumu Zhang It is certified that error appears in the above-identified patent and that said Letters Patent is hereby corrected as shown below:

Column 1,
Please add the following heading and paragraph from Line 12 and following:

--FEDERALLY SPONSORED RESEARCH AND DEVELOPMENT

This invention was made with support from the Government under Office of Naval Research Contract No. N00014-96-1-0733 and the National Science Foundation Grant No. CHE9712201. The Government has certain rights in the invention.--

Signed and Sealed this

Eleventh Day of March, 2008

JON W. DUDAS
*Director of the United States Patent and Trademark Office*